(12) United States Patent
Norenberg

(10) Patent No.: US 10,172,967 B2
(45) Date of Patent: *Jan. 8, 2019

(54) ANTICANCER THERAPY

(71) Applicant: STC.UNM, Albuquerque, NM (US)

(72) Inventor: Jeffrey P. Norenberg, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/427,355

(22) Filed: Feb. 8, 2017

(65) Prior Publication Data
US 2017/0304471 A1 Oct. 26, 2017

Related U.S. Application Data

(60) Continuation of application No. 14/669,313, filed on Mar. 26, 2015, now Pat. No. 9,610,371, which is a division of application No. 11/493,063, filed on Jul. 26, 2006, now abandoned.

(60) Provisional application No. 60/703,810, filed on Jul. 29, 2005, provisional application No. 60/764,043, filed on Jan. 31, 2006.

(51) Int. Cl.
| | |
|---|---|
| A61K 51/00 | (2006.01) |
| A61K 36/14 | (2006.01) |
| A61K 51/08 | (2006.01) |
| A61K 31/7068 | (2006.01) |
| A61K 38/31 | (2006.01) |
| A61K 45/06 | (2006.01) |

(52) U.S. Cl.
CPC .......... *A61K 51/08* (2013.01); *A61K 31/7068* (2013.01); *A61K 38/31* (2013.01); *A61K 45/06* (2013.01); *A61K 51/083* (2013.01); *A61K 51/088* (2013.01)

(58) Field of Classification Search
CPC ...... A61K 51/00; A61K 51/08; A61K 51/083; A61K 45/00; A61K 45/06; A61K 31/00; A61K 31/7068; A61K 38/00; A61K 38/31
USPC .... 424/1.11, 1.65, 1.69, 9.1, 9.2; 514/1, 1.1, 514/19.2, 19.3, 19.4, 19.5, 19.6, 7.1; 530/300, 311
See application file for complete search history.

(56) References Cited

U.S. PATENT DOCUMENTS

| | | |
|---|---|---|
| 4,938,949 A | 7/1990 | Borch et al. |
| 5,057,302 A | 10/1991 | Johnson et al. |
| 5,214,316 A | 5/1993 | Nagai |
| 5,428,154 A | 6/1995 | Gansow et al. |
| 5,650,134 A | 7/1997 | Albert et al. |
| 5,932,189 A | 8/1999 | Dean et al. |
| 6,051,554 A | 4/2000 | Hornik et al. |
| 6,077,668 A | 6/2000 | Kool |
| 6,316,414 B1 | 11/2001 | Burman et al. |
| 6,358,491 B1 | 3/2002 | Lister-James et al. |
| 6,930,088 B2 | 8/2005 | Hornik et al. |
| 7,122,622 B2 | 10/2006 | Macke et al. |
| 7,202,330 B2 | 4/2007 | De Jong et al. |
| 9,610,371 B2 * | 4/2017 | Norenberg ............. A61K 51/08 |
| 2004/0115203 A1 | 6/2004 | Dadachova et al. |

OTHER PUBLICATIONS

Bauer et al., Life Sci. 31, 1133-40 (1982).
Brazeau, et al., Science 129, 77-79 (1973).
Cai et al., Proc. Natl. Acad. Sci. USA 83, 1896-1900 (1986).
Corness et al., FEBS Lett. 321, 279-284 (1993).
De Jong et al., Q. J. Nucl. Med. 43, 356-366 (1999).
Epelbaum, Prog. Neurobiol., 27, 63-100 (1986).
Fueger et al., J. Nucl. Med. 43, 1856-62 (2001).
Gibril et al., Ann. Intern. Med. 125, 26-34 (1996).
Giusti et al., Eur. J. Clin. Invest. 27, 277-284 (1997).
Gurney, Clin. Oncol., 14, 2590-2611. (date not provided).
Halmos et al., J. Clin. Endocrinol Metab., 85, 3509-12 (2000).
Heppeler, et al., Curr. Med. Chem. 7, 971-994 (2000).
Hertel et al., Cancer Res. 50, 4417-4422 (1990).
Hofland et al., Proc. Assoc. Am. Physicians 111:63-69 (1999).
Hofland et al., J. Nucl. Med. 46, Suppl. 1, 191S-8S (2005).
Jensen et al., J. Clin. Endocrinol. Metab., 85(10), 3507-8 (2000).
Kaltsas, Endocr. Relat. Cancer 2005; 12:683-99.
Kath et al., Recent Results Cancer Res. 153, 23-43 (2000).
Krenning et al., Eur. J. Nucl. Med., 20, 716-731 (1993).
Lamberts et al., N. Engl. J. Med. 334, 246-254 (1996).
Nagy et al., Proc. Natl. Acad. Sci. USA 95, 1794-9 (1998).
Pauwels et al., Oncologist 10, 34-51 (2005).
Patel, Front. Neuroendocrinol. 20, 157-98 (1999).
Rens-Domiano et al., J. Neurochem, 58, 1987-96 (1992).
Reubi, Endocr. Rev. 24, 389-427 (2003).
Reubi, et al., Cancer Res. 47, 5758-64 (1987).
Reubi, et al. Eur. J. Pharmacol. 5, 45-9 (2002).
Reubi,et al., Metabolism 41, 104-10 (1992).
Rosenberg, et al., Cancer J. Surg. 34, 223-229 (1991).
Schally, Anticancer Drugs 5, 115-30 (1994).
Shimon, Endocrine 20, 265-9 (2003).
Stiefel et al., Support Care Caner 1:57-58 (1993).
Szekeres, et al., Crit. Rev. Clin. Lab. Sci. 34, 503 (1997).
Teunissen, et al. J. Nucl. Med. 2005; 46 Suppl 1:107S-14S.
Tolis, et al., Eur. J. Cancer, 35, 797-808 (1999).
Valkema , et al. , J. Nucl. Med. 2005; 46 Suppl 1:83S-91S1.
Veber, et al., Nature 292, 55-8 (1981).
Wermuth, et al., Pure and Applied Chemistry 70, 1129-1143 (1998).
Yamada, et al., Proc. Natl. Acad. Sci USA 89, 251-255 (1992).

(Continued)

*Primary Examiner* — D. L. Jones
(74) *Attorney, Agent, or Firm* — Henry D. Coleman; R. Neil Sudol

(57) ABSTRACT

A subject afflicted with a cancer or precancerous condition is treated by administering an agent that increases expression of somatostatin receptors, and a cytotoxic recognition ligand. In an alternative embodiment, somatostatin analogs, which are radiolabeled are used to treat cancer or precancerous conditions.

8 Claims, 17 Drawing Sheets

Specification includes a Sequence Listing.

(56) References Cited

OTHER PUBLICATIONS

Yamada, et al, Biochem. Biophys. Res. Commun. 195, 844-852 (1993).

Melis M, Vegt E, et al. Nephrotoxicity in mice after repeated imaging using 111In-labeled peptides. J Nucl Med. Jun. 2010; 51(6):973-7.

Rolleman EJ, Melis M, et al. Kidney protection during peptide receptor radionuclide therapy with somatostatin analogues. Eur J Nucl Med Mol Imaging. May 2010;37(5):1018-31.

De Jong M, Breeman WA, et al. Tumor imaging and therapy using radiolabeled somatostatin analogues. Acc Chem Res. Jul. 21, 2009; 42(7):873-80.

Kwekkeboom DJ, de Herder WW, et al. Treatment with the radiolabeled somatostatin analog [177 Lu-DODTA 0,Tyr3] octreotate: toxicity, efficacy, and survival. J Clin Oncol. May 1, 2008;26(13):2124-30.

Rolleman EJ, Krenning EP, et al. Long-term toxicity of [(177)Lu-DOTA (0), Tyr (3)]octreotate in rats. Eur J Nucl Med Mol Imaging. Feb. 2007;34(2):219-27.

Kwekkeboom DJ, Teunissen JJ, et al. Radiolaeled somatostatin analog [177Lu-DOTA0,Tyr3]octreotate in patients with endocrine gastroenteropancreatinc tumors. J Clin oncol. Apr. 20, 2005;23(12):2754-62.

Pauwels S, Barone R, et al. Practical dosimetry of peptide receptor radionuclide therapy with (90)Y-labeled somatostatin analogs. J Nucl Med. Jan. 2005;46 Suppl 1 :92S-98S.

De Jong M, Valkema R, et al. Somatostatin receptor-targeted radionuclide therapy of tumors: preclinical and clinical findings. Semin Nucl Med. Apr. 2002;32(2):133-40.

Valkema R, De Jong M, et al. Phase I study of peptide receptor radionuclide therapy with [In-DTPA]octreotide: the Rotterdam experience. Semin Nucl Med. Apr. 2002; 32(2):110-22.

Walrand S, Barone R, et al. Experimental facts supporting a red marrow uptake due to radiometal transchelation in (90)Y-DOTATOC therapy and relationship to the decrease of platelet counts. Eur J Nucl Med Mol Imaging. Feb. 12, 2011. E-pub ahead of print.[ 2011; 38:1270-1280.].

Walrand S, Jamar F, et al, 4-Step renal dosimetry dependent on cortex geometry applied to 90Y peptide receptor radiotherapy: evaluation using a fillable kidney phantom imaged by 90Y PET. J Nucl Med. Dec. 2010;61(12):1969-73.

Menda Y, O'Dorisio MS, et al. Phase I trial of 90Y-DOTATOC therapy in children and young adults with refractory solid tumors that express somatostatin receptors. J. Nucl Med. Oct. 2010; 51(10):1524-31.

Sierra ML, Agazzi A, et al. Lymphocytic toxicity in patients after peptide-receptor radionuclide therapy (PRRT) with 177Lu-DOTATATE and 90Y-DOTATOC. Cancer Biother Radiopharm. Dec. 2009:24(6):659-65.

Bodei L, Cremonesi M, et al. Long-term evaluatin of renal toxicity after peptide receptor radionuclide therapy with 90Y-DdDOTATOC and 177Lu-DOTATATE: the role of associated risk factors. Eur J Nucl Med Mol Imaging. Oct. 2008;35 (10):1847-56.

Miederer M, Henriksen G, et al. Preclinical evaluation of the alpha-particle generator nuclide 225Ac for somatostatin receptor radiotherapy of neuroendocrine tumors. Clin Cancer Res. Jun. 1, 2008;14(11):3555-61.

Barone R, Walrand S, et al. Therapy using labeled somatostatin analogues: comparison of the absorbed doses with 111In-DTPA-D-Phe1-octreotide and yttrium-labelled DOTA-D-Phe1-Tyr3-octreotide. Nucl Med Commun. Mar. 2008;29 (3):283-90.

Frilling A, Weber F, et al., Treatment with (90)Y- and (177)Lu-DOTATOC in patients with metastatic neuroendocrine tumors. Surgery. Dec. 2006; 140(6):968-76.; Discussion 976-7.

Forrer F, Waldherr C, et al. Targeted radionuclide therapy with 90Y-DOTATOC in patients with neuroendocrine tumors. Anticancer Res. Jan.-Feb. 2006;26(1B):703-7.

Forrer F, Uusijarvi H, et al. Treatment with 177Lu-DOTATOC of patients with relapse of neuroendocrine tumors after treatment with 90Y-DOTATOC. J Mud Med. Aug. 2005; 46(8):1310-6.

Barone R, Borson-Chazot F, et al. Patient-specific dosimetry in predicting renal toxicity with (90)Y-DOTATOC: relevance of kidney volume and dose rate in finding a dose-effect relationship. J Nucl Med. Jan. 2005; 46:46 Suppl 1:99S-106S.

Pless M, Waldherr C, et al., Targeted radiotherapy for small cell lung cancer using 90Yttrium-DdOTATOC, an Yttrium-labelled somatostatin analogue: a pilot trial. Lung Cancer. Sep. 2004:45(3):365-71.

Bodei L, Handkiewicz-Junak D, et al, Receptor radionuclide therapy with 90Y-DOTATOC in patients with medullary thyroid carcinomas. Cancer Biother Radiopharm Feb. 2004:19(1):65-71.

Bushnell D, Menda Y, et al, Assessment of hepatic toxicity from treatment with 90Y-SMT 487 (OctreoTher ™) in patients with diffuse somatostatin receptor positive liver metastases. Cancer Biother Radiopharm Aug. 2003: 18 (4):581-8.

Paganelli G, Bodei L, et al., 90Y-DOTA-D-Phe1-Tyr3-octreotide in therapy of neuroendocrine malignancies. Biopolymers 2002; 66(6):393-8.

Waldherr C, Pless M. et al, The clinical value of [90Y-DOTA]-D-Phe1-Tyr3-octreotide (90Y-DOTATOC0 in the treatment of neuroendocrine tumours: aa clinical phase II study. Ann Oncol. Jul. 2001; 12:941-5.

Otte A, Herrmann R, et al., Yttrium-90 DOTATOC: first clinical results. Eur J Nucl Med. Nov. 1999; 26(11):1439-47.

Bernard BF, Krenning EP, et al., D-Lysine reduction of indium-111 octreotide and yttrium-90 octreotide renal uptake. J Nucl Med . Dec. 1997; 38(12):1929-33.

Lamberts, SWJ et al., Octreotide; New England Journal of Medicine 1996; 334:246-254.

Behr TM, et al.; High-Linear Energy Transfer (LET) alpha versus Low-LET beta Emitters in Radioimmunotherapy of Solid Tumors: Therapeutic Efficacy and Dose-limiting Toxicity of Bi-213 versus Y-90 labelled CO17-1A Fab' Fragments in a Human Colonic Cancer Model. Cancer Research 1999; 59:2635-2643.

Norenberg JP, et al..; Bi-213-[DOTA0, Tyr3] Octreotide Peptide Receptor Radionuclide Therapy of Pancreatic Tumors in a Preclinical Animal Model. Clinical Cancer Research 2006; 12:897-903.

Nayak et al.; Cancer Biotherapy & Radiopharmaceuticals, Feb. 2005, vol. 20 (1), pp. 52-57.

* cited by examiner

ANTICANCER THERAPY

CROSS-REFERENCES TO RELATED APPLICATIONS

This patent application claims priority to U.S. Provisional Patent Application U.S. Ser. No. 60/703,810, filed Jul. 29, 2005, entitled "Radioisotopic Therapeutic Agent and Method" and U.S. Provisional Patent Application U.S. Ser. No. 60/764,043, filed Jan. 31, 2006, entitled "Combination Anticancer Therapy," each of which is hereby incorporated by reference in its entirety for all purposes.

GOVERNMENT FUNDING

The invention was made with government support under Grant No. DE-FG01-001NE23554, awarded by the United States Department of Energy, and Grant No. DHHS/PHS/NIH/NCRR/GCRC, MO1 RR00997, awarded by the National Institutes of Health National Center for Research Resources. The U.S. Government has certain rights in this invention.

BACKGROUND OF THE INVENTION

Somatostatin is a 14-amino acid peptide hormone (somatostatin-14; SS-14) found in many cells, particularly those of neuroendocrine origin, that acts as a neurotansmitter in the central nervous system. Reubi et al., Cancer Res. 47, 5758-64 (1987). There is also a somatostatin variant released by β cells in the pancreatic islets that is a 28 amino acid peptide (somatostatin-28; SS-28). Somatostatin has an inhibitory effect on growth hormone, and a generally antiproliferative effect. Somatostatin receptors (SSTR or SSR) are found on the surface of human tumor cells, including cells with amine precursor uptake and decarboxylation properties, such as pituitary tumors, endocrine pancreatic tumors, carcinoids, paragangliomas, small cell lung cancers, medullary thyroid carcinomas and pheochromocytomas. Reubi et al., Metabolism, 41, 104-10 (1992); Patel, Front. Neuroendocrinol. 20, 157-98 (1999). Somatostatin receptors belong to the guanine nucleotide-binding regulatory protein (G-protein)-linked receptor family.

Synthetic somatostatin analogs such as octreotide and lanreotide have been used for antitumor treatment and cancer detection. Jensen et al., J. Clin. Endocrinol. Metab., 85(10), 3507-8 (2000). Analogs of somatostatin were developed because human somatostatin has a very short half-life in circulation (2-3 minutes) and is easily broken down by endogenous peptidases. Rens-Domiano et al., J. Neurochem, 58, 1987-96 (1992). Somatostatin analogs typically, but need not, retain two important molecular features of somatostatin: its cyclic form and the 4 amino acids involved in the binding to the somatostatin receptor (i.e., amino acids 7-10 of the somatostatin sequence). A number of radiolabeled somatostatin analogs (e.g., [$^{111}$In-DTPA-DPhe$^1$]octreotide) have been developed that can be used to image these tumors using somatostatin receptor scintigraphy. Krenning et al., Bur. J. Nucl. Med., 20, 716-731 (1993). Somatostatin receptor scintigraphy is the most sensitive method to localize the primary and metastatic disease in subjects with all pancreatic endocrine tumors and carcinoids. Gibril et al., Ann. Intern. Med. 125, 26-34 (1996). The localization of these tumors by somatostatin receptor scintigraphy is due to the interaction of the radiolabeled analogs with specific cell surface somatostatin receptors.

Multiple subtypes of somatostatin receptors are known, and almost all neuroendocrine tumors (carcinoids, pancreatic endocrine tumors) possess at least one subtype, frequently multiple subtypes. Somatostatin receptor subtypes ($sst_1$, $sst_2$, $sst_3$, $sst_4$, and $sst_5$) have been isolated and cloned. Both octreotide and lanreotide have high affinity for somatostatin receptor sybtypes $sst_2$ and $sst_5$, lower affinity for $sst_3$ and very low affinity for $sst_1$ and $sst_4$. Patel, Front. Neuroendocrinol. 20, 157-198 (1999). Radiolabeled analogs of octreotide are rapidly internalized and the radiolabeled peptides can remain present in the cells for prolonged periods. Hofland et al., Proc Assoc Am Physicians. 111:63-69 (1999).

Radiotherapy using high doses of [$^{111}$In-DTPA-D-Phe$^1$] octreotide (DTPA: diethylenetriaminepentacetic acid), which emits auger and conversion electrons, as well as $^{90}$yttrium-labeled somatostatin analogs coupled by a DOTA (1,4,7,10-tetraazacyclododecane-1,4,7,10-tetraacetic acid) chelator, which can emit β-particles and give high radiation doses of greater penetrance, have been reported to inhibit tumor growth in both animal studies and in preliminary human studies. deJong et al., Q. J. Nucl. Med. 43, 356-366 (1999). Additional examples of somatostatin analogs that are being evaluated for use in the radionuclide therapy of tumors include [DOTA$^0$, Tyr$^3$] octreotide (DOTATOC) labeled with $^{131}$I, $^{90}$Y or $^{177}$Lu. Peptide receptor radionuclide therapy (PRRT) using radiolabeled DOTATOC has led to tumor responses in the majority of subjects, but has also posed problems with regard to renal and hematological toxicity. Reubi, Endocr. Rev. 24, 389-427 (2003). Another synthetic somatostatin-receptor targeting analog, [DOTA$^0$, Tyr$^3$]octreotate (DOTATATE) labeled with $^{177}$Lu has recently been investigated for PRRT. J, Nucl. Med. 2005 January; 46 Suppl 1:107S-14S; J Nucl Med. 2005 January; 46 Suppl 1:83S-91S1 Endocr Relat Cancer. 2005 December; 12(4): 683-99.

Despite good imaging and diagnostic results with $^{111}$In labeled [DTPA$^0$] octreotide (Octreoscan®) in the last few years, there have been several reports describing new somatostatin radioligands for studying sst expression. Some like [DOTA$^0$, Tyr$^3$] octreotide (DOTATOC) labeled with $^{131}$I, $^{90}$Y and $^{177}$Lu are also being evaluated for use in the radionuclide therapy of tumors (7). The new Peptide Receptor Radionuclide Therapy (PRRT) using radiolabeled DOTATOC has led to tumor responses in the majority of patients, but has also posed problems with renal and hematological toxicities Reubi, Endocr. Rev. 24, 389-427 (2003). In previous studies, kidney failures have been reported after treatment with DOTATOC labeled to β$^-$ particle emitter $^{90}$Y (8-10). In previously completed clinical studies, it was observed that 10% to 34% patients had complete remission following $^{90}$Y-DOTATOC treatment (11). The results of these studies illustrate the partial treatment potentials of this agent and the possible higher relapse rates that may occur in the future (12). The primary challenges that $^{90}$Y or $^{177}$Lu labeled DOTATOC faces are renal toxicities and incomplete treatments, especially in radio-resistant tumors.

Recent studies indicate that the presence of somatostatin receptors on other more common non-endocrine tumors may also be used for tumor localization or treatment. Halmos et al., J Clin Endocrinol Metab., 85, 3509-12 (2000). Increased densities of somatostatin receptors are found in various tumors of the central nervous system (meningiomas, astrocytomas, gliomas), some malignant lymphoid tumors (Hodgkin's disease, non-Hodgkin's disease), and in some cancers of the prostate, breast, kidney, liver, and lung. Jensen et al., J. Clin. Endocrinol. Metab., 85(10), 3507-8 (2000). Somatostatin analogs have been shown to have antiproliferative effects on breast, gastric, colorectal, prostate, thyroid and lung tumors, and cytotoxic somatostatin analogues have been shown to inhibit growth of human breast cancer, prostate cancer, renal cell carcinomas, and human glioblastomas. Kath et al., Recent Results Cancer Res. 153, 23-43 (2000); Froidevaux et al., Curt. Med. Chem. 7, 971-994 (2000). The effect of chemotherapeutic agents on the expression of somatostatin receptors has been investigated using pancreatic tumor cells. Fueger et al., J. Nucl. Med. 42(12), 1856-62 (2001).

Gemcitabine (2',2'-difluoro-2'-deoxycytidine; dFdC) is a pyrimidine analog that has shown activity in various solid tumors, including non-small cell lung cancer (NSCLC), small cell lung cancer, head and neck squamous cell cancer, germ cell tumors, lymphomas (cutaneous T-cell and Hodgkins' disease), mesothelioma, and tumors of the bladder, breast, ovary, cervix, pancreas, and biliary tract, as well as some hematologic malignancies. The compound was first reported by Lilly Research Laboratories, Eli Lilly and Co.; Indianapolis, Ind. Hertel et al., Cancer Res. 50, 4417-4422 (1990). Gemcitabine is a deoxycytidine analog with structural similarities to cytarabine (Ara-C).

Gemcitabine is metabolized intracellularly by nucleoside kinases to the active diphosphate (dFdCDP) and triphosphate (dFdCTP) nucleoside metabolites. The cytotoxic effect of gemcitabine is generally attributed to the actions of diphosphate and the triphosphate nucleosides, which lead to inhibition of DNA synthesis. Gemcitabine diphosphate (dFdCDP) inhibits ribonucleoside reductase, which is responsible for catalyzing the reactions that generate the deoxynucleoside triphosphates for DNA synthesis. Inhibition of this enzyme by the diphosphate nucleoside causes a reduction in the concentration of the deoxynucleotides, including dCTP. Gemcitabine triphosphate (dFdCTP) competes with dCTP for incorporation into DNA. The reduction in the intracellular concentration of dCTP (by the action of the diphosphate) further enhances the incorporation of gemcitabine triphosphate into DNA, a process referred to as self-potentiation. After the gemcitabine nucleotide is incorporated into DNA, only one additional nucleotide is added to the growing DNA strand. Further DNA synthesis is inhibited, as DNA polymerase epsilon is unable to remove the gemcitabine nucleotide and repair the growing DNA strand, resulting in what is known as masked chain termination. Gemcitabine induces an S-phase arrest in the cell cycle, and triggers apoptosis in both human leukemic cells and solid tumors. Tolis et al., Eur. J. Cancer, 35, 797-808 (1999). In addition to its cytotoxic effect, gemcitabine is a potent radiosensitizer. Gemcitabine has been investigated as a radiosensitizer for rodent and human tumor cells, including those found in pancreatic, non-small cell ung, head and neck, colorectal, breast, and cervical cancer. Pauwels at al., Oncologist 10(1), 34-51 (2005).

OBJECTS OF THE INVENTION

It is an object of the invention to provide novel compounds and pharmaceutical compositions for the treatment of cancer and precancerus conditions.

It is another object of the invention to provide methods for treating precancerous conditions or cancer using compounds according to the present invention.

It is an additional object of the invention to provide methods for treating precancerous conditions or cancer using compounds which enhance expression of somatostatin receptors in cancer cells in combination with agents which bind to somatostatin receptors to deliver cytotoxic agents.

Any one of these and/or other objects of the invention may be readily gleaned from a review of the description of the invention which follows.

SUMMARY OF THE INVENTION

The present invention provides a therapy effective for treating a subject afflicted with a cancer or precancerous condition. According to a first embodiment, the therapy includes administration of a radiopharmaceutical composition such as a somatostatin analog labeled with a high Linear-Energy-Transfer (LET) α-emitter. An example of the radiopharmaceutical composition is $^{213}$Bi-DOTATOC, but may be any somatostatin analog, preferably selected from octreotide, lanreotide and vapreotide which have been radiolabelled with a Linear-Energy-Transfer (LET) α-emitter, preferably using a chelating moiety. In this method, the radiolabeled somatostatin analog is administered to a patient in need of treatment in an effective amount to reduce the likelihood that a precancerous condition will develop into cancer, to inhibit the growth of cancer or tumor and/or shrink the cancer or tumor in the patient or reduce the likelihood of metastasis of the cancer and/or tumor in the patient. Remission of cancer in the patient is an alternative result in the present method.

According to another embodiment, the therapy is a combination therapy involving administering a first therapeutic agent that increases expression of somatostatin receptors, and a second therapeutic agent that selectively binds to a somatostatin receptor on the cancer cell and delivers a cytotoxic compound or moiety to the cancer cell. An example of the first therapeutic agent is gemcitabine or an active gemcitabine metabolite. The second therapeutic agent may include a recognition ligand that targets the somatostatin receptor, and a cytotoxic compound. Administration of the second therapeutic causes a deleterious effect on the cancerous or precancerous cell. An example of a second therapeutic agent is a radiolabelled somatostatic analog, such as $^{213}$Bi-DOTATOC, among numerous others.

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such.

BRIEF DESCRIPTION OF THE FIGURES

FIG. 13A. Graph represents the high uptake organs, showing localization in the pancreas and adrenals was significantly higher in the non-tumor. FIG. 13B. Graph represents the low uptake organs, showing localizations were significantly higher in both the stomach and muscle.

DETAILED DESCRIPTION OF ILLUSTRATIVE EMBODIMENTS

Figure 1:
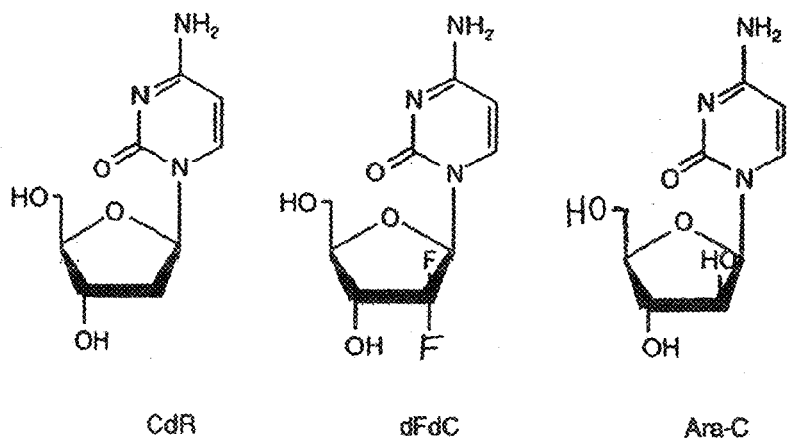
FIG. 1 provides structural formulas for deoxycytidine (CdR), cytarabine (Ara-C), and gemcitabine (dFdC).

The following terms shall be used to describe the present invention.

The term "patient" is used throughout the specification to describe an animal, generally a mammal and preferably a human, to whom treatment, including prophylactic treatment, with the compositions according to the present invention is provided. For treatment of those infections, conditions or disease states which are specific for a specific animal such as a human patient, the term patient refers to that specific animal. While the use of the present invention to treat humans represents a primary aspect of the invention, veterinary applications are also intended.

The term "effective" is used herein, unless otherwise indicated, to describe an amount of a compound or composition which, in context, is used to produce or effect an intended result, whether that result relates to the treatment of a tumor including a carcinogenic tumor or other cancer or the treatment of a precancerous lesion or other cell(s) which express abnormal or foreign proteins or immunogens on a cell surface. In certain aspects related to the coadministration of a compound according to the present invention with another anticancer agent, the present invention relates to the enhancement of the anti-cancer effect of the anti-cancer compound. In instances where enhancement of the expression of somatostatin receptors represents an aspect of the present invention, the term effective refers to an amount of a compound which appreciably or substantially increases the expression of somatostatin receptors in cancer cells. This term subsumes all other effective amount or effective concentration terms which are otherwise described in the present application. With respect to an anti-cancer effect, that effect may be one or more of inhibiting further growth of tumor or cancer cells, reducing the likelihood or eliminating metastatsis or producing cell death in the tumor or cancer cells, resulting in a shrinkage of the tumor or a reduction in the number of cancer cells or preventing the regrowth of a tumor or cancer after the patient's tumor or cancer it in remission.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Representative cancers include, for example, stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, leukemia, melanoma, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others, which may be treated by one or more compounds according to the present invention.

The term "tumor" is used to describe a malignant or benign growth or tumefacent.

The term "precancerous" refers to a state in which cells are growing in an uncontrolled manner and where that growth has yet to develop into a cancerous growth.

The term "anti-cancer compound" or "anti-cancer agent" is used to describe any compound (including its derivatives) which may be used to treat cancer. Anti-cancer agents as described hereunder are a subset of cytotoxic agents which may be used in the present invention. Exemplary anti-cancer compounds for use in the present invention for linking with a somatostatin ligand include anti-metabolite agents which are broadly characterized as antimetabolites, inhibitors of topoisomerase I and II, alkylating agents and microtubule inhibitors (e.g., taxol), as well as tyrosine kinase inhibitors (e.g., surafenib), EGF kinase inhibitors (e.g., tarceva or erlotinib) and ABL kinase inhibitors (e.g. gleevec or imatinib). Anti-cancer compounds for use in the present invention include, for example, Aldeslcukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; gleevec (imatinib); goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; surafenib; talbuvidine (LDT); talc; tamoxifen; tarceva (erlotinib); temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof, among others. Note that one of ordinary skill in the art may readily link a ligand which binds to a somatostatin receptor with an anti-cancer agent as described hereunder for purposes of treating cancer.

The term "coadministration" or "combination therapy" is used to describe a therapy in which at least two active compounds in effective amounts are used to treat cancer or another disease state or condition as otherwise described herein at the same time. Although the term coadministration preferably includes the administration of two active compounds to the patient at the same time, it is not necessary that the compounds be administered to the patient at the same time, although effective amounts of the individual compounds will be present in the patient at the same time. Compounds according to the present invention may be administered with one or more anti-cancer agent, including antimetabolites, alkylating agents, topoisomerase I and topoisomerase II inhibitors as well as microtubule inhibitors, among others. Anticancer compounds for use in the present invention include those described above, and mixtures thereof, among others. Coadministration of one of the present compounds with another anticancer agent as otherwise described herein will often result in a synergistic enhancement of the anticancer activity of the other anticancer agent, an unexpected result. One or more of the present compounds may also be coadministered with another bioactive agent (e.g., antiviral agent, antihyperproliferative disease agent, agents which treat chronic inflammatory disease, among others or as otherwise described herein).

The term "somatostatin receptor" refers to 5 distinct somatostatin receptors (SSTR1-SSTR5) in various target tissues. See, Brazeau, et al., Science, 129, 77-79 (1973); Epelbaum., Prog. Neurobiol., 27, 63-100 (1986); Yamada, et al., Proc. Natl. Acad. Sci. USA, 89, 251-255 (1992); Comess, et al., FEBS Lett., 321, 279-284 (1993); and Yamada, et al., Biochem. Biophys. REs. Commun., 195, 844-852 (1993). All 5 human SSTR subtypes bind SST-24 and SST-28 with high affinity and belong to the superfamily of guanine nucleotide binding protein-coupled receptors. In the present invention, the single term "sonatostatin receptor" refers to the panoply of somatostatin subtypes unless a particular tissue and expression of a particular subtype in such tissue is referred to. In the case of a particular tissue, the term somatostatin receptor refers to somatostatin receptors which are found in that type of cancer tissue.

According to a first embodiment, the present invention provides a radiopharmaceutical composition and method for treating a subject afflicted with a cancer or precancerous condition by administering of a somatostatin analog radiolabeled with a high Linear-Energy-Transfer (LET) α-emitter. Examples of high LET α-emitters include $^{211}$At, $^{213}$Bi, $^{177}$lutetium, and $^{111}$indium. In preferred aspects of the invention, the somatostatin analog is octreotide, lanreotide or vapreotide, which is chelated to any one of $^{211}$At, $^{213}$Bi, $^{177}$lutetium, and $^{111}$indium, preferably $^{213}$Bi. This compound may be administered along or in combination (coadministration) with another anticancer agent.

$^{213}$Bi decays mainly (98%) by β$^-$-emission, with a 440-keV γ-emission and a half life ($t_{1/2}$) of 45.6 minutes to the ultra-short-lived high-energy (8.375-MeV) α-emitter $^{213}$Po ($t_{1/2}$=4.2 microseconds). $^{213}$Bi also has a direct decay pathway (2%) by α-emission to the (3.980 MeV) β$^-$-particle emitter $^{209}$Tl (16). Accordingly, in one embodiment, the present invention provides a somatostatin analog [DOTA0 Tyr3]octreotide (DOTATOC) labelled $^{213}$Bi.

Radionuclides such as $^{213}$Bi that emit alpha particles offer radiotherapeutic advantages as they emit much higher energy particles than most of the betas, and yet their ranges are typically two orders of magnitude lower. Alpha particles have a high LET that is about 100 times greater than the beta particles, manifested by a higher RBE and a much shorter range. Consequently, a much greater fraction of total energy is imparted to the targeted cancer cell and thus very few nuclear hits are required to kill the cell (24, 25, 26).

An exemplary method of preparation will now be described. $^{213}$Bi can be readily obtained from an "in-house" $^{225}$Ac/$^{213}$Bi radionuclide generator system (National Institutes of Health, National Cancer Institute, Bethesda, Md.). Prior to each elution, the $^{225}$Ac generator column was first rinsed with distilled water and then flushed with air to remove the water. In order to selectively elute the $^{213}$Bi daughter, the column was eluted with 10 milliliter of 0.1 M hydrochloric acid. The eluate was diluted with water at 5.6 times the eluate volume of water (56 milliliter). This dilution was loaded onto a MP-50 cation-exchange column. This column was then reverse eluted with an additional 0.4 milliliter of freshly prepared 0.1 M hydroiodic acid that contained the desired $^{213}$Bi.

Freshly eluted $^{213}$Bismuth (4 MBq) was added to 0.5 µg of DOTATOC solution and incubated for 5 minutes at 100° C. in a hot block. Prior to heating, the pH of the final solution was adjusted to 6 to 7 using 3 M NH$_4$OAc solution.

Incorporation yield (IC) was assessed using Silica Gel instantaneous thin layer chromatography (ITLC) with 0.9% sodium chloride as the mobile phase. The radiolabeled samples were diluted with 4 mM diethylenetriamine pentaacetic acid (DTPA) at pH=4.1. Five microliter of the diluted sample was spotted on an ITLC silica gel strip and allowed to develop in a chromatographic chamber. Upon completion of the migration to the solvent front, the ITLC sample strips were allowed to dry, cut in half and counted on a Wallac Wizard gamma counter (Perkin Elmer, Boston, Mass.) to determine the IC. Radiochemical purity (RCP) was assessed via high performance liquid chromatography (HPLC) analysis. The liquid chromatography system (Thermo Separation Products, San Jose, Calif.) consisted of a multisolvent-delivery pump, an auto sampler, a radiometric detector (γ-RAM, IN/US Systems, Inc., Tampa, Fla.), and a $C_{18}$, 5 μm, 4.6×250 mm, reverse-phase HPLC column. The mobile phase consisted of Buffer A: 0.5 M Ammonium Acetate in HPLC grade water, pH 5.5 and Buffer B: 100% HPLC grade methanol. The HPLC samples were analyzed with a 1:10 dilution in 4 mM DTPA. The flow rate was 1.0 milliliter per minute and the retention time for the radiolabeled product was 14.0 to 14.5 minutes.

The radiolabeled product, $^{213}$Bi-DOTATOC, was incubated at 37° C. in a $CO_2$ incubator for 1 hour in rat serum obtained from a male Lewis rat to study in vitro stability. After incubation the product was analyzed by the ITLC and HPLC methods previously described. The radiolabeling incorporation yields and radiochemical purity by ITLC and HPLC were greater than 99.9V % and greater than 95%, respectively. $^{213}$Bi-DOTATOC demonstrated acceptable stability and was unchanged after 1 hour of in vitro incubation in rat serum. The biodistribution data demonstrated specific binding to sst expressing tissues.

As will be described in greater detail below, it should be appreciated that the high LET α-emitter radiolabeled somatostatin analog of the present invention may be administered to a patient using any known technique.

According to still another embodiment, the present invention further provides a pharmaceutical composition and method for treating a subjected afflicted with a cancer or precancerous condition by administering a therapeutic agent comprising $^{213}$Bi and a pharmaceutically acceptable carrier. The therapeutic agent may further include a targeting moiety that targets the therapeutic agent to a selected mammalian cell. Those of skill in the art will be familiar with suitable targeting moieties and will be aware that the specific targeting moiety used will be dependant upon various factors including, for example, the mammalian cell that is selected. Accordingly, the targeting moiety may be a ligand or ligand analog that is configured to bind to a receptor that is expressed or preferentially expressed on the selected mammalian cell. Furthermore, the targeting moiety may be configured to facilitate internalization of the therapeutic agent by the cell.

Accordingly, the therapeutic agent may include a peptide, peptide analog, peptide derivative, or a peptidomimetic compound. The therapeutic agent may further be effective in peptide receptor radionuclide therapy (PRRT).

Accordingly, where the selected cell is a cancer cell, the targeting moiety may be a somatostatin peptide, analog, or derivative thereof. Alternatively, the targeting moiety may include an octreotide or analog or derivative thereof, including vapreotide or lanreotide.

According to another embodiment, the present invention further provides a method of treating a subject afflicted with a cancer or precancerous condition by increasing the expression level of somatostatin receptors in the cancer cells and administering a therapeutic agent that binds to the somatostatin receptors of the cancer. The expression level of somatostatin receptors in the cancer cells of the subject is optionally increased by administering a first therapeutic agent that increases somatostatin receptor expression in the cancer cells. Administration of a second therapeutic agent that binds to somatostatin receptors of the cancer provides a cytotoxic compound that has a deleterious effect on the cancer. Increasing the level of somatostatin receptors on the cancer of the subject provides advantages such as, for example, facilitating association of the second therapeutic agent with the cancer, and potentially decreasing the amount of the second therapeutic agent necessary to provide the desired level of antitumor activity.

First Therapeutic Agent

According to an embodiment, a first therapeutic agent is administered to the subject in order to increase the expression level of somatostatin receptor in the cancer cells. Somatostatin receptors are proteins with an affinity for the hormone somatostatin, and include at least five different receptor subtypes. The first therapeutic agent may be effective to increase the expression level of a particular somatostatin receptor subtype (e.g., $sst_1$-$sst_5$) or it may increase the expression of a plurality of somatostatin receptor subtypes. The increase in expression of somatostatin receptors may occur immediately upon exposure to the first therapeutic agent, or it may occur after a certain period of time. For example, somatostatin receptor expression levels may increase about 1, 2, 3, or 4 days after initial exposure to the first therapeutic agent.

An increase in expression level of somatostatin receptors in the cancer cells can be evidenced by an increase in the number of somatostatin receptors in the cancer cells and/or the affinity of the somatostatin receptors for their ligand, compared to the number and/or affinity of somatostatin receptors found in the cancer in the absence of administration of the first therapeutic agent. Preferably, the somatostatin receptors are expressed on the surface of the cancer cells where they may readily bind the second therapeutic agent. An increase in expression level of somatostatin receptors may include stimulation of expression of somatostatin receptors on cancer cells that previously did not express somatostatin receptors, in addition to increased expression of somatostatin receptors by cells that previously expressed somatostatin receptors at a lower level. In an additional aspect of the invention, somatostatin receptor expression is increased to a higher extent in cancer cells relative to normal, non-neoplastic tissue.

The first therapeutic agent may increase the expression level of somatostatin receptors in the cancer in any of a variety of ways. For instance, in one embodiment of the invention, the first therapeutic agent may increase the expression level of somatostatin receptors in the cancer by inducing cell cycle arrest. Cell cycle arrest may occur during any of the cell cycle phases. For example, cell cycle arrest may occur in the G0/G1 phase, the G2/M phase, or the S phase. While not intending to be bound by theory, cell cycle arrest may lead to increased somatostatin receptor expression by retaining the cell in a phase in which somatostatin receptor is expressed. For example, somatostatin receptor expression may occur during the S phase in order to regulate cell growth. Cell cycle arrest in S phase may lead to an increase in somatostatin receptor expression. Cell cycle arrest may occur as the result of a variety of different effects. For instance, cell cycle arrest may occur as a result of the inhibition of DNA synthesis. DNA synthesis may be inhibited, for example, due to chain termination by incorporation of an altered nucleoside analog (e.g., dFdCTP), and/or by inhibition of an enzyme involved in DNA synthesis such as ribonucleotide reductase, which is a rate-limiting enzyme in DNA synthesis (e.g., via the activity of dFdCDP).

Accordingly, in some embodiments of the invention, the first therapeutic agent may be a DNA synthesis inhibiting agent. A wide variety of antitumor agents are known to those skilled in the art that inhibit DNA synthesis. For example, one class of DNA synthesis inhibiting agents are alkylating agents (e.g., classes of alkylating agents such as nitrogen mustards, aziridines, epoxides, nitrosoureas, triazines, and hydrazines).

According to one embodiment of the invention, the first therapeutic agent is a DNA synthesis inhibiting agent which is a nucleoside analog (e.g., a purine or pyrimidine analog). Nucleoside analogs include compounds wherein, for example, the sugar or base is chemically modified. Many "analogous" forms of purines and pyrimidines are known in the art, an many of them are in use as chemotherapeutic agents. Purine analogs include, for example, mercaptopurine, azathioprine, thioguanine, deoxocoformycin, fludarabine, cladribine, and hydroxyurea.

Pyrimidine is a nitrogen-containing, six-membered ring that is bonded to the C-1 position of ribose to form a pyrimidine nucleoside. Pyrimidine nucleotides in DNA include cytosine and thymine. Embodiments of the invention include analogs wherein a deoxyribose sugar of the pyrimidine analog includes halogen substituents at the 2-deoxy portion of the sugar. The halogen used may be fluorine, chlorine, bromine, or iodine. For example, in one embodiment of the invention, the pyrimidine analog includes fluorine substituents at the 2-deoxy position (e.g., 2',2'-difluoro-2'-deoxycytidine (gemcitabine)). Pyrimidine analogs include, for example, 5-fluorouracil, cytosine arabinoside, 5-azacytidine, and gemcitabine.

Typically, purine or pyrimidine analogs are active only after metabolic conversion to the active nucleotide form. These nucleotide analogs may thus not only may be incorporated into DNA but also can mimic the natural effector compounds in regulatory pathways.

An exemplary but not exhaustive list of nucleoside analogs can be found in U.S. Pat. No. 6,989,452 and includes 4-acetylytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, $N^6$-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyluracil, 5-methoxyaminomethyl-2-thiouracil, □-D-mannosylqueosine, 5-methoxycarbonylmethyluracil, 5-methoxyuracil, 2-methylthio-$N^6$-isopentenyladenine, uracil-5-oxyacetic acid methylester, uracil-5-oxyacetic acid (v), wybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid (v), pseudouracil, queosine, 2-thiocytosine, and 2,6-diaminopurine. In addition, the conventional bases may be replaced by halogenated bases. Furthermore, the 2'-furanose position on the base can have a non-charged bulky group substitution. Examples of non-charged bulky groups include branched alkyls, sugars and branched sugars. See also U.S. Pat. No. 6,077,668 for additional nucleoside and nucleotide analogs.

The DNA synthesis inhibiting agent may include a class of compounds that target a particular portion of DNA synthesis. For example, the DNA synthesis inhibiting agent may be a ribonucleotide reductase inhibitor. Examples of agents that may be used to inhibit ribonucleotide reductase include hydroxyurea, guanazole, gemcitabine, fludarabine, and thiosemicarbazone derivatives. Examples of suitable ribonucleotide reductase inhibitors are described by Szekeres et al. (Szekeres et al., Crit. Rev. Clin. Lab. Sci., 34, 503 (1997)).

The first therapeutic agent, in some embodiments of the invention, also includes active metabolites of the first therapeutic agent. For example, pyrimidine nucleoside analogs are typically activated by metabolic conversion to the active nucleotide, which may be a monophosphate, diphosphate, or triphosphate. Active metabolites, as defined herein, are metabolically formed analogs of an agent that play a role in the activity of the agent. The active metabolites of pyrimidine nucleoside analogs include phosphate derivatives of pyrimidine nucleoside analogs. For example, gemcitabine is metabolized intracellularly by nucleoside kinases to the active diphosphate and triphosphate nucleoside metabolites, and thus gemcitabine diphosphate and gemcitabine triphosphate are active metabolites included in embodiments of the invention. These gemcitabine metabolites play a role in the activity of gemcitabine through inhibition of ribonucleoside reductase (by gemcitabine diphosphate) and competition with dCTP for incorporation into DNA (by gemcitabine triphosphate).

Second Therapeutic Agent

The present invention may further include administration of a second therapeutic agent that binds to somatostatin receptors of the cancer. For instance, pre-treatment with a first therapeutic agent (e.g., gemcitabine) may be followed by administration of a second therapeutic agent, such as, but not necessarily limited to, the radiopharmaceutical compositions described above. The second therapeutic agent may include a recognition ligand that binds to a somatostatin receptor, but does not significantly bind to other cell surface components. Binding of the recognition ligand to a somatostatin receptor may bring the second therapeutic agent into proximity with a cancer cell. The second therapeutic agent may further include a cytotoxic agent that has a deleterious effect on the cancer when the second therapeutic agent is brought into proximity with a cancer cell. In addition to bringing the cytotoxic agent into proximity with the cancer cell, interaction of the second therapeutic agent with the somatostatin receptor may facilitate uptake of the second therapeutic agent into the cell. Hofland et al., J. Nucl. Med. 46, Suppl. 1, 191S-8S (2005).

The second therapeutic agent may include a recognition ligand that selectively binds to somatostatin receptors. A recognition ligand that "selectively binds" a somatostatin receptor is one that will, under appropriate (e.g., physiological) conditions, interact with a somatostatin receptor preferentially compared to other cell surface components, such as non-somatostatin receptors. Recognition ligands include somatostatin analogs, antibodies, and other types of proteins, peptides, small organic molecules, and the like that selectively bind to somatostatin receptors. Recognition ligands may bind to all subtypes of somatostatin receptors, or they may selectively bind to one or more somatostatin receptor subtypes. For example, embodiments of the invention include recognition ligands that selectively bind to somatostatin receptor subtype $sst_2$. Examples of recognition ligands that bind to specific somatostatin receptor subtypes are described by Reubi et al. (Reubi et al., *Eur. J. Pharmacol.*, 5, 45-9 (2002).

Antibodies

The recognition ligand may take the form of an antibody that selectively binds to somatostatin receptors. Antibodies, as defined herein, include vertebrate antibodies, hybrid antibodies, chimeric antibodies, humanized antibodies, altered antibodies, univalent antibodies, monoclonal and polyclonal antibodies, Fab proteins, scFv single chain domain, scFv dimers of single chain domain or diabodies, minibodies, bi-specific minibodies, and aggregates of targeting domains. Monoclonal and polyclonal anti-somatostatin receptor antibodies are well known to the art. For example, commercially available polyclonal antibodies that are derived from rabbit, and having specific epitopes for SSTr subtype 1, 2, 4, and others are available from Abcam Inc., Cambridge, Mass.

Somatostatin Analogs

Alternatively, or additionally, the recognition ligane may take the form of somatostatin or a somatostatin analog. Somatostatin is generally expressed as a tetradecapeptide, and is the natural recognition ligand for somatostatin receptors. The tetradecapeptide form of somatostatin has the amino acid sequence of Ala-Gly-Cys-Lys-Asn-Phe-Phe-Trp-Lys-Thr-Phe-Thr-Ser-Cys (SEQ ID NO:1). While somatostatin itself may be used as a recognition ligand, synthetic somatostatin analogs, which incorporate a Phe-D-Trp-Lys-Thr (or similar sequence) and which are metabolically stabilized at both the N- and C-terminals, have been developed for clinical applications. For example, three commercially available somatostatin analogs (i.e. octreotide [D-Phe-Cys-Phe-D-Trp-Lys-Thr-Cys-Thr-OH); OCT (Rosenberg et al., Cancer J. Surg. 34, 223-229 (1991)], lanreotide [D-☐Nal-Cys-Tyr-D-Trp-Lys-Val-Cys-Thr-NH$_2$; LAN (Giusti et al., Eur. J. Clin. Invest. 27, 277-284 (1997))] and vapreotide [D-Phe-Cys-Tyr-D-Trp-Lys-Val-Cys-Trp-NH$_2$; VAP (Stiefel et al., Support Care Cancer 1:57-58 (1993))]) have been shown to be effective in controlling the growth of some human tumors. These SST analogs all have similar binding profiles for four of the five human sst subtypes (i.e. a high affinity for human sst2 and sst5, moderate affinity for human sst3, and very low affinity for human sst1), but LAN and VAP have a moderate affinity for human sst4, whereas OCT has little or no affinity for this human sst (for review, see Lamberts et al., N. Engl. J. Med. 334, 246-254 (1996)).

Figure 2:
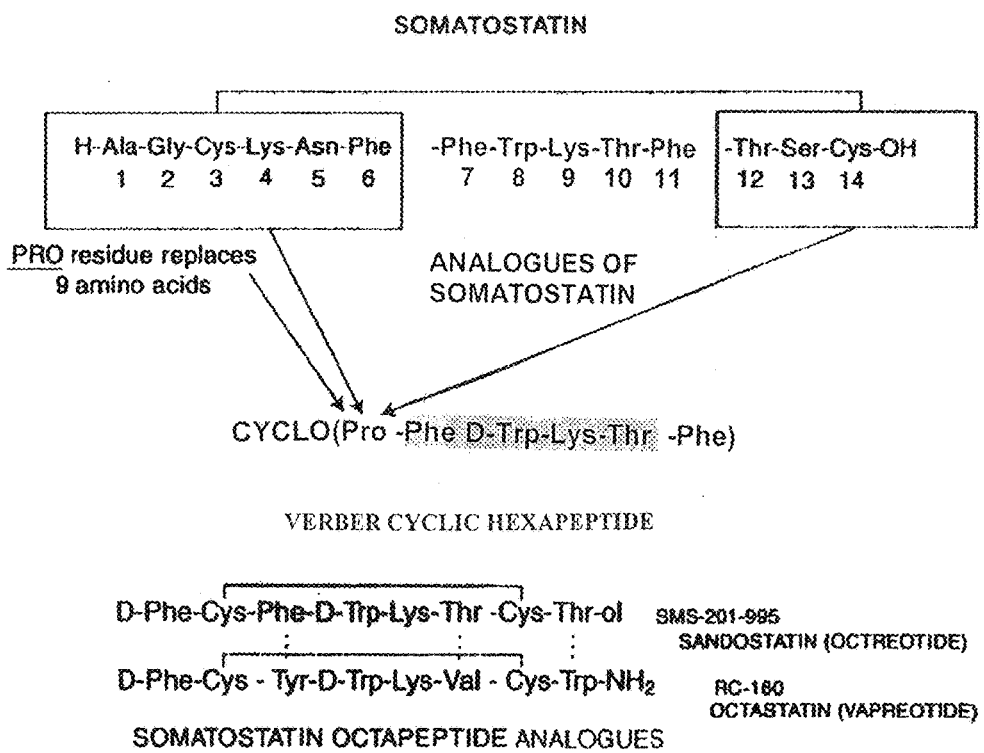
FIG. 2 illustrates the structural relationship between somatostatin and three somatostatin analogs, as shown in Cancer Medicine, 6$^{th}$ edition (Frei et al., eds., Hamilton, Canada, 2003).

In one embodiment, a somatostatin analog includes amino acids 7-10, or derivatives or analogs thereof such as D-amino acids, of somatostatin, since this sequence is thought to be important for providing affinity for the somatostatin receptor. See Veber et al., Nature 292, 55-8 (1981). For example, Veber et al. describe the preparation of a number of cyclic hexapeptide somatostatin analogs in which nine of somatostatin's amino acids are replaced with a single proline amino acid, while Bauer et al. describe the preparation of a series of octapeptide cysteine-bridged analogs of somatostatin (Bauer et al., Life Sci, 31, 1133-40 (1982)). FIG. 2 illustrates the structural relationship between somatostatin, the Veber hexapeptide, and the octapeptide analogs octreotide and vapreotide. Accordingly, some embodiments of the invention include the use of somatostatin analogs that include 5-10 amino acids, or more preferably 6-8 amino acids. According to some embodiments, these somatostatin analogs include the binding region amino acids from positions 7 to 10 of somatostatin.

Examples of octapeptide somatostatin analogs suitable for use as recognition ligands in embodiments of the invention include octreotide (D-Phe-Cys-Phe-D-Trp-Lys-Thr-Cys-Thr-OH), lanreotide (D-βNal-Cys-Tyr-D-Trp-Lys-Val-Cys-Thr-NH$_2$) and vapreotide (D-Phe-Cys-Tyr-D-Trp-Lys-Val-Cys-Trp-NH$_2$). Many additional somatostatin analogs have been synthesized that are suitable for use as recognition ligands. See Schally A V. Anticancer Drugs 5, 115-30 (1994); Cai et al., Proc. Natl. Acad. Sci. USA, 83, 1896-900 (1986); Shimon, L, Endocrine, 20, 265-9 (2003). See also U.S. Pat. Nos. 6,051,554; 6,214,316; 5,932,189; 6,358,491; 6,316,414; and 6,930,088, relevant portions of which are incorporated herein. While somatostatin analogs are typically peptides, non-peptide somatostatin analogs have also been developed and may be used in embodiments of the invention. Non-peptide somatostatin analogs include somatostatin peptidomimetics, which are compounds containing non-peptidic structural elements that are capable of mimicking or antagonizing the biological action of natural somatostatin. Peptidomimetics typically lack classic peptide characteristics such as, for example, enzymatically scissile peptidic bonds. See the IUPAC definition of a peptidomimetic compound. Wermuth et al., Pure and Applied Chemistry, 70, 1129-1143 (1998).

As stated above, the second therapeutic agent may also include a cytotoxic compound. For the purposes of the present disclosure, a cytotoxic compound is one that has a deleterious effect on a cell, such as causing cell death, inhibition of cell growth and/or interfering with the cell's ability to divide. The cytotoxic compound is brought into proximity of the cancer cells by use of the recognition ligand, as described above, and has a deleterious effect on proximal cancer cells. The deleterious effect may include, for example, direct cytotoxicity, cytostasis, or apoptosis. A wide variety of cytotoxic agents are available and known to those skilled in the art. A cytotoxic agent is a substance that is potentially genotoxic, oncogenic, mutagenic, teratogenic or in any way hazardous to a cell. Cytotoxic agents may include, for example, antitumor agents, toxic agents such as ricin, and radionuclides. Other examples include bacterial toxins (e.g., Pseudomonas exotoxin), ricin A-chain, daunorubicin, doxorubicin, 2-pyrrolinodoxorubicin, methotrexate, and ribosome inhibitors (e.g., trichosantin). An example of a suitable second therapeutic agent is a cytotoxic agent such as doxorubicin or 2-pyrrolinodoxorubicin linked to an octapeptide somatostatin analog. See Nagy et al, Proc. Natl. Acad. Sci. USA 95, 1794-9 (1998). Additional cytotoxic somatostatin analogs are described by Hofland et al. (Hofland et al., J. Nucl. Med. 46, Suppl. 1, 191S-8S (2005)). Other cytotoxic agents (anticancer) agents have been discussed hereinabove. One or more of these traditional cytotoxic agent may be modified so that they are linked to the somatostatin recognition ligand, either covalently or through chelation. Alternatively, these anticancer agents may be coadministered with the first therapeutic compound and the second therapeutic compound to further treat cancer according to the present invention.

The cytotoxic compound included in the second therapeutic agent may be a radionuclide. Radionuclides provide a deleterious effect on cancer cells through release of high energy particles such as α-, β-, and γ-particles. A wide variety of radionuclides suitable for use as a cytotoxic compound are known to those skilled in that art. Examples include $^{67}$gallium, $^{68}$gallium, $^{71}$arsenic, $^{72}$arsenic, $^{65}$zinc, $^{76}$bromine, $^{201}$thallium, $^{99m}$technicium, $^{48}$vanadium, and $^{49}$vanadium, as well as radionuclides more typically used in therapeutic applications such as $^{90}$yttrium, $^{111}$indium, $^{177}$lutetium, $^{225}$actinium, $^{209}$bismuth, $^{212}$bismuth, $^{213}$bismuth, $^{64}$copper, $^{67}$copper, $^{76}$arsenic, $^{77}$arsenic, $^{203}$lead, $^{209}$lead, $^{212}$lead, $^{166}$holmium, $^{153}$promethium, $^{186}$rhenium, $^{188}$rhenium, and $^{211}$astatine.

Radionuclides that release high-linear energy transfer (LET) α-particles may be used and are preferable, as these particles are highly toxic but have a relatively short range (e.g., two orders of magnitude lower than β-particles) and are thus less likely to damage non-proximal tissue. Examples of radionuclides suitable for use as the cytotoxic compound include $^{213}$bismuth, $^{177}$lutetium, and $^{111}$indium.

In addition to cytotoxic agents which are inherently toxic, cytotoxic agents which require external activation to become cytotoxic may also be used. These include cytotoxic agents that are chemically, enzymatically, or electromagnetically activated. For example, somatostatin analogs including an attached superparamagnetic nanoparticle could be used, wherein the superparamagnetic nanoparticle becomes cytotoxic upon exposure of the nanoparticle to electromagnetic radiation, e.g., causing thermal ablation.

The cytotoxic compound and the recognition ligand of the second therapeutic agent may be associated together in any of a variety of ways. The association between the cytotoxic compound and the recognition ligand can be covalent or non-covalent. For example, the cytotoxic compound and the recognition ligand may be non-covalently associated by imbedding them together in a structure such as a liposome. Alternatively, the cytotoxic compound may be covalently bound to a recognition ligand through reaction between the cytotoxic agent and the recognition ligand. For example, to covalently bind somatostatin analog octapeptides to doxorubicin, conjugation was performed by coupling using N-9-fluorenylmethoxycarbonyl (N-Fmoc). Nagy et al., Proc. Natl. Acad. Sci. USA., 17, 1794-9 (1998). Other coupling agents that may be used include dicyclohexyl carbodiimide and n-hydroxy succinamide.

Chelating agents that bind to the cytotoxic compound can be used to associate the cyotoxic agents to a recognition ligand. Use of chelating agents is often preferred when associating inorganic compounds such as radionuclides with recognition ligands. A variety of chelating agents are available that may be used to associate the cytotoxic compound to the recognition ligand. Examples of bifunctional chelating agents (i.e., chelating agents that include an array of metal-binding groups plus a moiety capable of covalent binding to a protein substrate) include chelating proteins, diethylenetriamine-pentaacetic acid (DTPA), imino-diacetic acid (IDA), nitrilo-triacetic acid (NTA), ethylenediamine tetraacetic acid (EDTA), diaminocyclohexame-tetraacetic acid (DCTA), porphyrin, deferoxamine, tctraagacyclo-tetradecane-tetraacetate (TETA), and 1,4,7,10-tetraazacyclododecane-1,4,7,10-tetraacetic acid (DOTA). It is to be understood that the invention is not intended to be limited to a particular chelating agent used. Rather, one of skill in the art can select a chelating agent based on the compound, such as the metal or radionuclide, to be incorporated and the clinical objectives as well as the compatability of the chelating agent with the chemistry associated with the ligand. Exemplary classes of chelates include open-chain polyaminocarboxylates, such as EDTA (ethylenediaminetetraacetic acid) and DTPA (diethylenetriaminepentaacetate); AZA macrocyclics such as cyclen (1,4,7,10-tetraazacyclododecane), cyclam (1,4,8,11-tetraazacyclotetradecane), bridged-cyclam (1,4,8,11-tetraazabicyclo[6.6.2]hexadecane), et-cyclam (1,4-ethano-1,4,8,11-tetraazacyclotetradecane), cylamdione (3,9-dioxy-1,4,8,11-tetraazacyclotetradecane), and diamsar (1,8-diamino-3,6,10,13,16,19-hexaazabicyclo(6,6,6)eicosane); polyaminocarboxylic macrocycles such as DOTA: (1,4,7,10-tetraazacyclodoccane-1,4,7,10-tetraacetic acid), TRITA: (1,4,7,10-tetraazacyclotridecane-1,4,7,10-tetraacetic acid), TETA: (triethylenetetramine), bridged-cyclam-2a: (1,4,8,11-tetraazabicyclo[6.6.2]hexadecane-1,8-di (methanephosphonic acid)), DO3A: (1,4,7-tris (carboxymethyl)-1,4,7,10-tetraazacyclododecane), DO2A: (1,4,7,10-tetraazacyclododecane-1,7-bis(acetic acid)); and polyaminophosphonate macrocycles such as DOTP: (1,4,7,10-tetraazacyclododecane-1,4,7,10-tetra(methanephosphonic acid)), DO3P: (1,4,7,10-tetraazacyclododecane-1,4,7-tri (methanephosphonic acid)), and DO2P: (1,4,7,10-tetraazacyclododecane-1,7-di(methanephosphonic acid)).

An example illustrating the structure and function of a chelating agent is provided by DTPA, which includes a backbone of three nitrogen atoms linked by two ethylene chains. Extending from the nitrogen atoms on the backbone are five carboxymethyl moieties. The carboxymethyl groups may be reacted using conventional peptide chemistry to form an amide bond with an amino acid residue present on an antibody or other protein molecule. The other four carboxymethyl moieties, together with the three nitrogen atoms, then remain available for metal binding. See, for example, U.S. Pat. No. 5,057,302.

DOTA is a particularly suitable chelating agent for use with many metal ion radionuclides such as bismuth, lutetium, and indium. DOTA may be synthesized by alkylating cyclen with chloroacetic acid or bromoacetic acid, and forms especially stable complexes with lanthanides, which are retained by the chelating agent with very high kinetic stability. DOTA may be readily bound to a recognition ligand using, for example, the DOTA-tris(tert-butyl ester). Examples of recognition ligands coupled to radionuclides using DOTA, for use as second therapeutic agents, include $^{111}$lutetium coupled to octreotide ($^{177}$Lu-DOTATOC) and $^{213}$bismuth coupled to octreotide ($^{213}$Bi-DOTATOC), as described further in the examples herein.

While not intending to be bound by theory, in addition to its functional role in coupling a cytotoxic compound to a recognition ligand, chelating agents may also play a role in the antitumor activity of the second therapeutic agent by providing resistance to degradation or by functioning as a scavenger subsequent to uptake by the cancer cell.

A particularly preferred second therapeutic agent is described in U.S. provisional patent application U.S. Ser. No. 60/703,810, filed Jul. 29, 2005, entitled "Radioisotopic Therapeutic Agent and Method" and in Appendix A hereto.

Antitumor Therapy

According to some embodiments, the present invention provides a method of treating a subject afflicted with a cancer or precancerous condition by administering a therapeutic agent that binds to the somatostatin receptors of the cancer cell and delivers a cytotoxic agent that has a deleterious effect on the cancer. The method may further comprise increasing the expression level of somatostatin receptors in the cancer cell prior to administering the cytotoxic agent.

The cancer that is treated using the present methods may be primary cancer or it may be metastatic cancer. The present methods are suitable for the treatment of any cancer or precancerous condition in which somatostatin receptors are expressed by the cancer cells. Somatostatin receptors are generally expressed in higher levels by cancer cells relative to the cells of normal tissue. Preferably, the cancer cells bear a greater number of somatostatin receptors than are found in non-cancerous tissue. Somatostatin receptors have been demonstrated on the surface of a wide variety of cancer cells. In particular, somatostatin receptors have been demonstrated in cancers that include cancer cells with amine precursor uptake and decarboxylation properties. Furthermore, the present methods are particularly suitable for the treatment of any cancer or precancerous condition in which the expression level of somatostatin receptors in the cancer cells can be increased.

The invention is particularly well-suited for treatment of cancer tumors. Accordingly, in one embodiment, the present invention provides a method for treating a subject that is afflicted with a cancerous or precancerous tumor, such as a carcinoma, a sarcoma, or a lymphoma. Preferably, the cancer treated is one that has neural and/or hormonal responsiveness. Typically these cancers are referred to as "-omas." In an embodiment, the cancer treated is one that is treatable with gemcitabine either "on label" or "off label." Examples of such cancers include pancreatic cancer, breast cancer, small cell lung cancer, pituitary adenomas and other neuroendocrine carcinomas.

As noted earlier, increased densities of somatostatin receptors are found in various cancers of the central nervous system (meningiomas, astrocytomas, gliomas), some malignant lymphoid cancers (Hodgkin's disease, non-Hodgkin's disease), and in some cancers of the prostate, breast, kidney, liver, and lung, among others. Accordingly, embodiments of the invention may be directed to treatment of somatostatin-receptor expressing cancer cells. Cancers that have been found to express somatostatin receptors include a variety of different types of cancer, such as breast, pancreatic, gastric, prostate, renal, colorectal, thyroid, lung, kidney, liver, central nervous system, and malignant lymphoid cancers. Somatostatin receptor expression can be demonstrated at the mRNA level using a variety of methods, such as in situ hybridization, RNAse protection assays, reverse transcriptase polymerase chain reaction, or autoradiography. The presence of somatostatin receptors can also be demonstrated using other methods such as immunohistochemistry. In further embodiments of the invention, the method is used to treat tumors resulting from cancers of neuroendocrine origin such as somatotrophic tumors of the anterior pituitary and pancreatic islet-cell tumors.

Treating a subject may provide a reduction in tumor load or a decrease in tumor growth in a subject in response to administration of the first and second therapeutic agent. The reduction in tumor load may represent a direct decrease in tumor mass, or it may be measured in terms of tumor growth delay, which is calculated by subtracting the average time for control tumors to grow over to a certain volume from the time required for treated tumors to grow to the same volume. The subject is preferably a mammal, such as a domesticated farm animal (e.g., cow, horse, pig) or pet (e.g., dog, cat). More preferably, the subject is a human. The treatment may result in a decrease in the likelihood that precancerous tissue will develop into cancer. In addition, in preferred embodiments, the treatment may result in decreasing the likelihood that metastatis of the cancer will occur, and optimally results in remission of the treated cancer.

Administration and Formulation of Therapeutic Agents

Methods of administering small molecule therapeutic agents such gemcitabine are well-known in the art. Dosage calculation for antitumor agents are exemplified, for example, by Gurney. Gurney H., J. Clin. Oncol., 14, 2590-2611. Methods for extrapolation of effective dosages in mice, and other animals, to humans are also known in the art; for example, see U.S. Pat. No. 4,938,949. Dosage calculations for individual therapeutic agents may also be readily determined from the literature by those skilled in the art. For example, dosing and clinical studies of somatostatin analogs, gemcitabine, and numerous other drugs may be found at the U.S. Food and Drug Administration Center for Drug Evaluation and Research website, and from literature that accompanies commercially available therapeutic agents, such as product literature for GEMZAR (Eli Lilly and Company), the commercially available injectable form of gemcitabine HCL (PV 4046 AMP; Eli Lilly and Company, 2005).

For chemotherapeutic agents such as gemcitabine, dosages useful in the combination therapy of the invention include any dosage which is known to be useful or applicable for monotherapy using gemcitabine, or for other combination therapies that involve gemcitabine.

The therapeutic agents described in the present disclosure can be administered to a subject alone or together (coadministered, optionally, but not necessarily, in a single formulation) with other active agents as described herein, and are preferably administered with a pharmaceutically acceptable buffer. The therapeutic agents can be combined with a variety of physiological acceptable carriers, additives for delivery to a subject, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, alcohol, phosphate buffered saline, and other balanced salt solutions.

The formulations may be conveniently presented in unit dosage form and may be prepared by any of the methods well known in the art of pharmacy. Preferably, such methods include the step of bringing the therapeutic agent (i.e., the active agent) into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering the therapeutic agents to a subject in an amount effective to produce the desired effect. The therapeutic agents can be administered as a single dose or in multiple doses. Useful dosages of the active agents can be determined by comparing their in vitro activity and the in vivo activity in animal models.

In the embodiment in which a first therapeutic agent is administered to increasing receptor expression and a second therapeutic agent is administered that targets the receptors, the first and second therapeutic agents may be administered together or separately in a single dose or in multiple doses. Administration of the second therapeutic agent after administration of the first therapeutic agent provides the advantage of providing time for the first therapeutic agent to enrich somatostatin receptor expression in the cancer cells, thereby facilitating targeting of the second therapeutic agent to the cancer. The second therapeutic agent may be administered as much as two weeks after the administration of the first therapeutic agent or as little as two days afterward or even sooner, such as 24 hours after administration of the first therapeutic agent. In a preferred embodiment, the second therapeutic is administered about 3 to 6 days following the administration of the first therapeutic agent.

Moreover, treatment of a subject afflicted with a cancer or precancerous condition by administering a first and second therapeutic may result in an additive effect. More preferably, treatment by administering a first and second therapeutic agent results in a synergistic therapeutic effect. A synergistic effect, as defined herein, occurs when treatment by a first therapeutic agent in conjunction with a second therapeutic agent results in a reduction in tumor load or growth delay that is greater than the reduction in tumor load or growth delay that is observed when the effects of separate treatment by the first therapeutic agent and the second therapeutic agent of the invention are added together, where the dosages and treatment schedules are otherwise the same when used individually or in combination. The comparison of the combined treatment with the effects of separate treatment, added together, result in a ratio that will be greater than 1 (i.e., greater than 100%) if a synergistic effect is present. Preferably, a synergistic effect with a ratio of at least 2 (i.e., at least 200%) is provided by the method of the invention, and more preferably the synergistic effect has a ratio of at least 3 (i.e., at least 300%).

The therapeutic agents of the present invention are preferably formulated in pharmaceutical compositions and then, in accordance with the methods of the invention, administered to a subject, such as a human subject, in a variety of forms adapted to the chosen route of administration. For example, the therapeutic agents may be formulated for intravenous administration. The formulations may, however, include those suitable for oral, rectal, vaginal, topical, nasal, ophthalmic, or other parenteral administration (including subcutaneous, intramuscular, intraperitoneal and intratumoral, in addition to intravenous) administration.

Formulations suitable for parenteral administration conveniently include a sterile aqueous preparation of the active agent, or dispersions of sterile powders of the active agent, which are preferably isotonic with the blood of the recipient. Parenteral administration of the therapeutic agents (e.g., through an I.V. drip) is an additional form of administration. Isotonic agents that can be included in the liquid preparation include sugars, buffers, and sodium chloride. Solutions of the active agents can be prepared in water, optionally mixed with a nontoxic surfactant. Dispersions of the active agent can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the active agent, preferably by filter sterilization. Preferred methods for preparing powders include vacuum drying and freeze drying of the sterile injectible solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the active agents over a prolonged period can be achieved by including agents for delaying, for example, aluminum monostearate and gelatin.

Formulations of the present invention suitable for oral administration may be presented as discrete units such as tablets, troches, capsules, lozenges, wafers, or cachets, each containing a predetermined amount of the active agent as a powder or granules, as liposomes containing the first and/or second therapeutic agents, or as a solution or suspension in an aqueous liquor or non-aqueous liquid such as a syrup, an elixir, an emulsion, or a draught. Such compositions and preparations may contain at least about 0.1 wt-% of the active agent. The amounts of the therapeutic agents should be such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

The present invention is illustrated by the following examples. It is to be understood that the particular examples, materials, amounts, and procedures are to be interpreted broadly in accordance with the scope of the invention as set forth herein.

EXAMPLES

Single Radiolabelled Somatostatin Analog as Anti-Cancer Agent

Example 1

Toxicology was assessed at 25 days in 4 groups of tumor bearing male Lewis rats (average volume 0.75±0.3 mm). Rats in the first group, Cohort 1, were injected on day 1 only. Rats in second cohort were injected on days 1 and 2, while rats in the third cohort were injected on days 1, 2, and 3. Rats were injected with 2.56 µg, 0.5 µg, 0.5 µg DOTATOC, on day 1, day 2 and day 3, respectively, with a nominal activity of 3.7 MBq. Each dose was divided into 2 injections at 1 hour intervals. The rats received the following cumulative average activities per group: Cohort 1 (N=3) received 4.3±0.7 MBq, Cohort 2 (N=3) received 9.0±0.4 MBq, and Cohort 3 (N=4) received 12.6±0.3 MBq of $^{213}$Bi-DOTATOC. Cohort 4 (N=4) was added as control group and injected twice daily with unlabelled DOTATOC on three consecutive days.

After 24 days, the animals were put into a metabolic cage to collect urine samples for creatinine clearance analysis. Creatine clearance was determined as previously described (20). After 24 hour urine collection, the animals were euthanized with halothane. For blood collection, a cardiac puncture was performed. Blood analysis consisted of hemoglobin (Hgb), hematocrit (Hct), red blood cells (RBC's), and white blood cells (WBC's) with differential, and platelets (Pt's). Additionally T4 and FSH values were assessed using the serum.

Additional groups were then designed to study the effects of the treatment on a somatostatin receptor positive tumor. The first group was designed to study the effects of treatment on large volume tumors (average volume 1720±608 mm$^3$). This group, Cohort 5 (N=5), received three fractionated doses of $^{213}$Bi-DOTATOC (specific activity 7.4 MBq $^{213}$Bi/1 µG DOTATOC) with a total average cumulative dose of 13.0±0.5 MBq of $^{213}$Bi-DOTATOC. The last cohort, the sixth cohort (N=4), was injected with two fractionated doses, $^{213}$Bi-DOTATOC (specific activity 7.4 MBq $^{213}$Bi/1 µG DOTATOC) with a total average cumulative dose of 22.2±0.7 MBq of $^{213}$Bi-DOTATOC. As described earlier, each dose was divided into 2 injections separated by a 1 hour interval. Tumor response to the treatment was assessed in all cohorts by daily tumor measurements.

A 26 week toxicology study was performed in 3 groups of rats. The first group, Cohort 7 (N=3), received three fractionated doses $^{213}$Bi-DOTATOC (specific activity 7.4 MBq 213Bi/1 µG DOTATOC with a total average cumulative dose of 12.75±1.1 MBq. The second group, Cohort 8 (N=3), received D-lysine (concentration 400 mg/mL) immediately before receiving three fractionated doses $^{213}$Bi-DOTATOC with a specific activity 7.4 MBq $^{213}$Bi/1 µG DOTATOC with a total average cumulative dose of 11.39±0.14 MBq. The third group, cohort 9 (N=3) received 3 fractionated doses of DOTATOC. Rats were injected with 2.56 µg, 0.5 µg, 0.5 µg DOTATOC, on day 1, day 2 and day 3, respectively. As described earlier, each dose was divided into 2 injections separated by a 1 hour interval.

Pathology

Organs were harvested and immediately placed in 10% formalin for a minimum of 48 hours. Following fixation in formalin, bone samples were placed in decalcifying solution for 36 hours. Trimmed organs were sent to the TriCore Laboratories (Albuquerque, N. Mex.) where they were embedded in paraffin, sectioned, and stained with Hematoxylin and Eosin (H and E). Histopathologic evaluation was performed by a board certified veterinary pathologist (DFK) who examined the following organs of each animal: heart, lung, kidneys, testicles, spleen, pancreas, pituitary bone marrow, urinary bladder, adrenals, and two different sections of the liver.

Sections of both the right and left kidneys were examined to determine nephrotoxicity in all cohorts. Bone marrow was examined to evaluate hypoplasia and other lesions in Cohorts 3 and 4. Interstitial nephritis and bone marrow were scored as follows: 0 no lesions, 1 minimal lesions, 2 mild lesions, 3 moderate lesions, and 4 severe lesions.

Statistics

For the pathology scoring, to evaluate nephrotoxicity on the 6 treatment groups, a frequency analysis was performed in StatXact-5 using the Jonckheere-Terpstra Test. For all other data, graphs and calculations were performed in SigmaStat®-3 and SigmaPlot®-9 as well as Graph Pad Prism®-4 using the t-test. For all statistical tests results were considered significant when p<0.05. Animal biodistribution and tumor volume data are expressed as the average, plus or minus the SEM.

Results

Figure 13A:
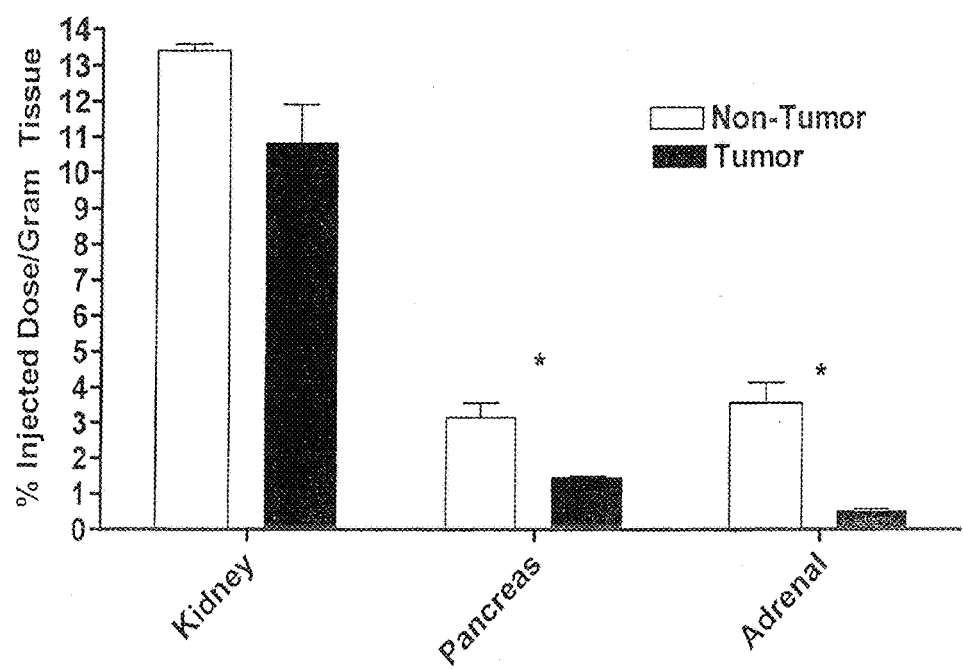
FIG. 13A, 13B: Graphical comparisons of Tumor and Non-Tumor Bearing Rats at 1 hour post injection of $^{213}$Bi-DOTATOC. Columns, means, Bars, SEM, white columns represent non-tumor bearing rats and black columns represent tumor bearing rats. Significance of $p<0.05$ is represented by a (*).
Figure 13B:
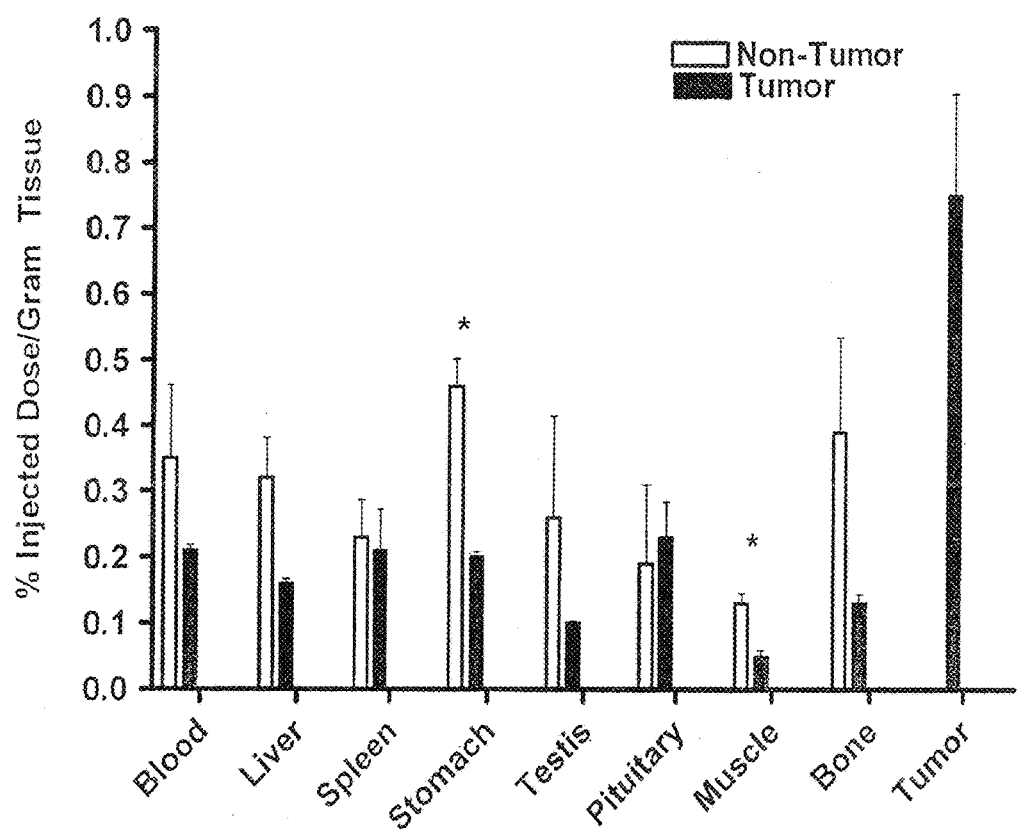

The radiolabeling incorporation yields and radiochemical purity by ITLC and HPLC were greater than 99.9% and greater than 95%, respectively. $^{213}$Bi-DOTATOC demonstrated acceptable stability and was unchanged after 1 hour of in vitro incubation in rat serum. The biodistribution data demonstrated specific binding to sst (somatostatin) expressing tissues. Administration of free $^{213}$Bi, compared to $^{213}$Bi-DOTATOC, resulted in higher accumulation of radioactivity in non-tumor bearing rats at 3 hours post injection in the kidneys (34.47±1.40% injected dose/gram vs. 11.15±0.46%, p<0.0001), the bone marrow (0.31±0.01% injected dose/gram vs. 0.06±0.02%, p<0.00023), the spleen (0.36±0.02% injected dose/gram vs. 0.08±0.01%, p<0.00053), the liver (0.50±0.05% injected dose/gram vs. 0.14±0.02% p<0.002), the blood (0.07±0.01% injected dose/gram vs. 0.02±0.00%, p<0.022), the testis (0.03±0.01% injected dose/gram vs. 0.02±0.00%, p<0.016) and the stomach (0.25±0.00% injected dose/gram vs. 0.08±0.01%, p<0.000015). Administration of $^{213}$Bi-DOTATOC in tumor bearing rats versus non-tumor bearing rats showed a decreased uptake at 1 hour in the pancreas (3.15±0.4% injected dose/gram vs. 1.44±0.05%, p<0.014) and the adrenals (3.55±0.57% injected dose/gram vs. 0.50±0.05%, p<0.0061) as shown in FIG. 13A.

Figure 14:
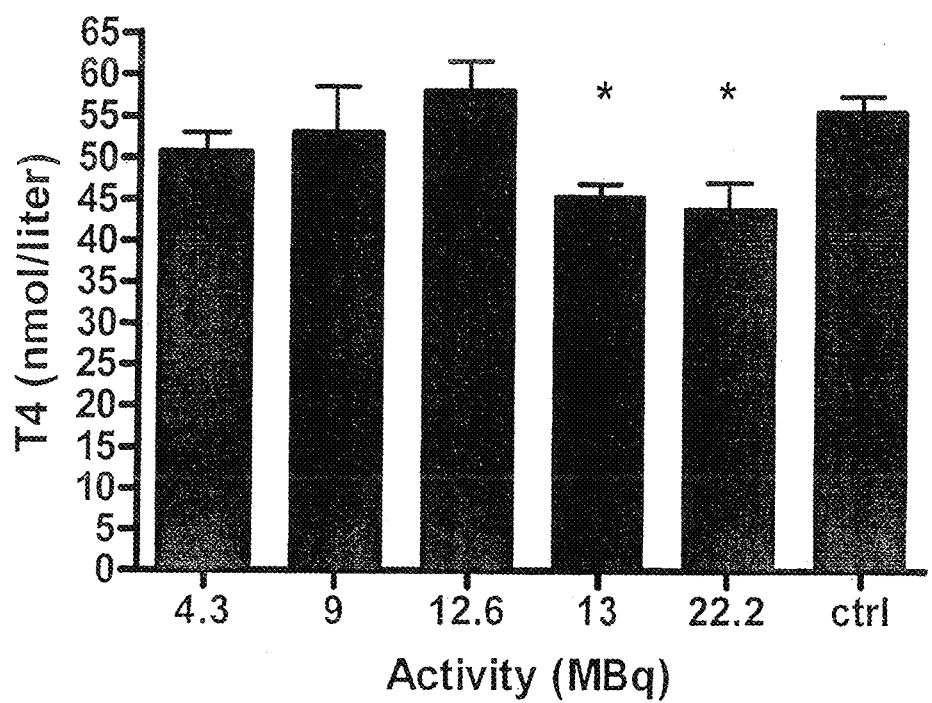
FIG. 14 is a graphical comparison of T4 values in serum taken from different treatment groups of $^{213}$Bi-DOTATOC at 25 days. Columns, means, Bars, SEM. Significance of $p<0.05$ is represented by a (*). Graph represents the decreased T4 value in (nmol/liter) with the increase of injected activity.

No difference in creatinine clearance was seen between the control group (DOTATOC only) and the bismuth treated animals for the 25 day study. Hematology results also did not show any significant differences between the control group and the bismuth treated animals. No significant changes were found in the FSH values between treated and control animals. However, significance was seen with T4 values between the two highest treatment groups 22.2 MBq (p<0.024) and 13.0 MBq (p<0.006) as compared to control (FIG. 14)

Figure 15:
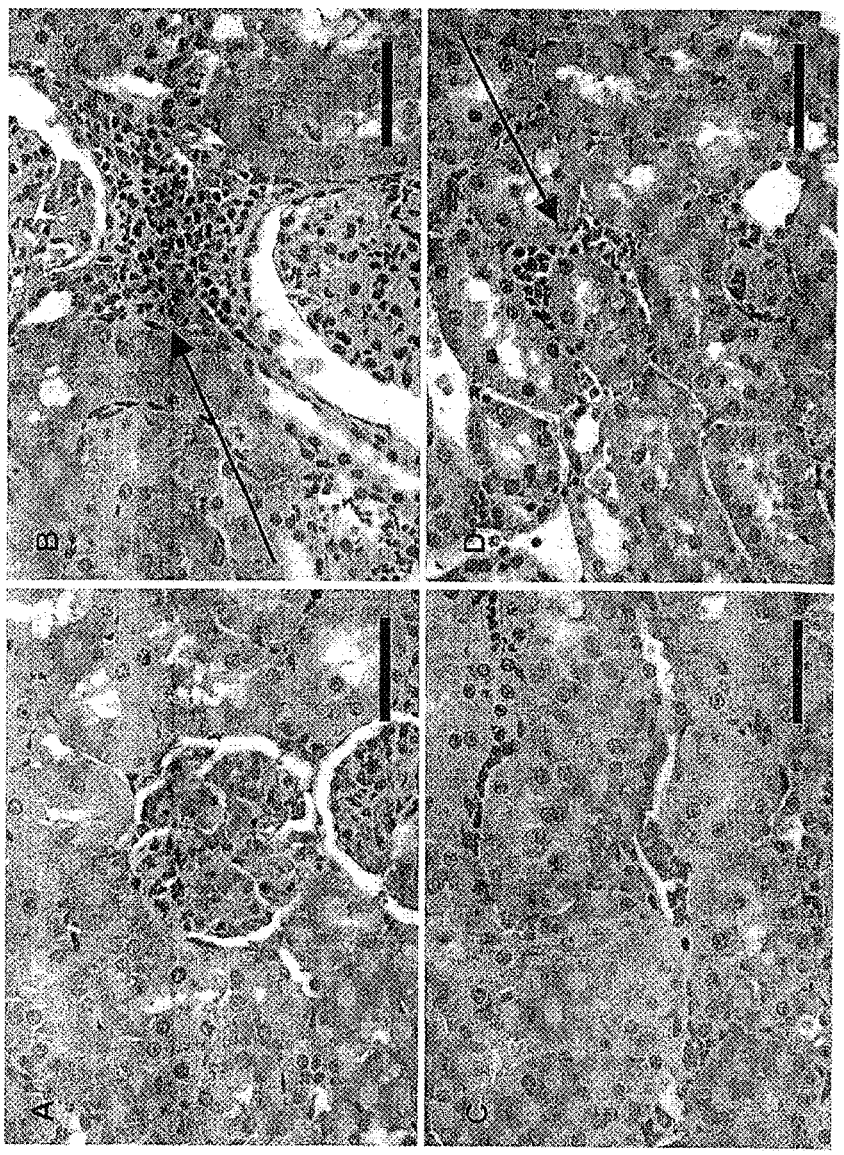
FIG. 15 shows that unaffected animals had normal-appearing glomeruli (A, upper left) and convoluted tubules (C, lower left), and no inflammatory cells were seen in the interstitium (A upper left, C lower left). Animals with interstitial nephritis had normal-appearing glomeruli (B, upper right) and tubules (D, lower right), but there were small aggregates of mononuclear inflammatory cells in the interstitium (arrows, upper and lower right). Kidney sections were stained with hematoxylin and eosin. Bar=50 μm.

The results of the bone marrow analysis for the DOTATOC control group versus the low dose (12.6 MBq) $^{213}$Bi-DOTATOC treatment group showed no lesions at 25 days; neither hypoplasia nor hyperplasia was observed. The average histopathologic score for nephritis for each treatment group was <1. Representative kidney sections of the treated animals are shown in FIG. 15. Statistical analysis of the data showed that the likelihood of interstitial nephritis increased with increasing dose when all treatment groups were analyzed (p<0.04 with the Jonckheere-Terpstra Test). This significance was lost when the high-dose treatment group (22.2 MBq) was eliminated. Minimal toxicity was seen in the high-dose treatment cohort, except for one kidney in this group, which showed mild interstitial nephritis (Table 1).

Histopathological examination revealed no evidence of treatment induced toxicity at 25 days in the heart, lungs, liver, spleen, and urinary bladder. No histopathologic abnormalities were seen in any of the animals in the testes, adrenals, or pancreas. Pituitary cysts were seen in 2 out of 4 animals in the high-dose (22.2 MBq) treatment group. However, such cysts are generally considered to be incidental findings in Lewis rats.

No difference in creatinine clearance was seen between the control group (DOTATOC only) and the bismuth treated animals for the 26 week study. Hematology results also did not show any significant differences between the control group and the bismuth treated animals. No significant changes were found in the FSH or T4 serum values between treated and control animals.

Histopathological examination at 26 weeks found minimal nodular cortical hyperplasia in both adrenals in all $^{213}$Bi-DOTATOC treated rats, while only 2 rats in the D-lysine cohort had one adrenal each with nodular cortical hyperplasia; no adrenal hyperplasia was seen in the control cohort. Microcystic pancreatic degeneration, ranging from mild to moderate was seen in all of the cohorts. Cardiomyopathy was seen in one rat in the $^{213}$Bi-DOTATOC group, 2 rats in the D-lysine group, and no rats in the control group. All groups contained some rats with mild to moderate microcystic degeneration in the pituitary. In the Bi-DOTATOC cohort, 83% of the kidneys had minimal to mild interstitial nephritis, while the Lysine and the controls cohorts had 67%. All groups showed some mild or moderate cholangiohepatitis and perivasculitits in the liver. Animals in most groups, including the control groups had minimal to mild interstitial pneumonia.

Figure 16:
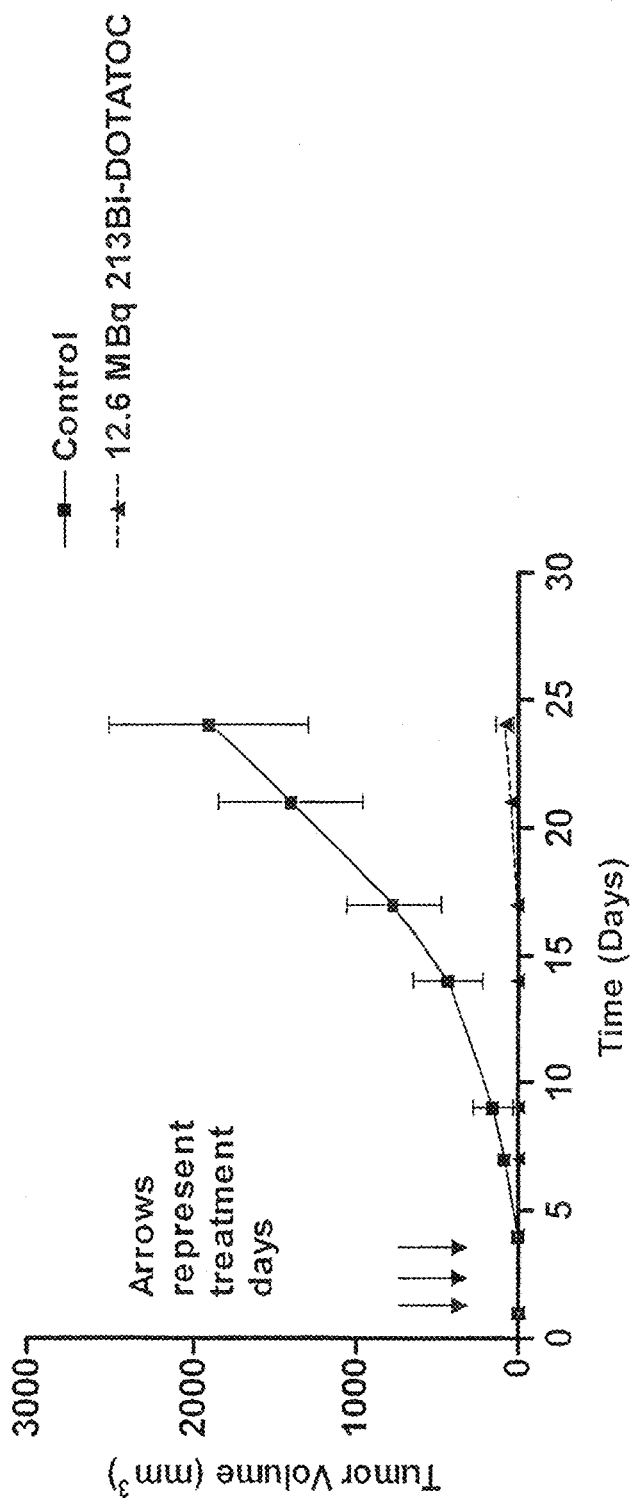
FIG. 16 shows a graph of small volume tumor bearing Lewis rats given DOTATOC alone or a total 12.6 MBq of $^{213}$Bi-DOTATOC. Symbols, means, Bars, SEM, Solid line with the square symbol represents the control, dashed line with the triangle symbol represents 12.6 MBq $^{213}$Bi-DOTATOC. Rats were treated for 3 consecutive days with DOTATOC or $^{213}$Bi-DOTATOC.
Figure 17:
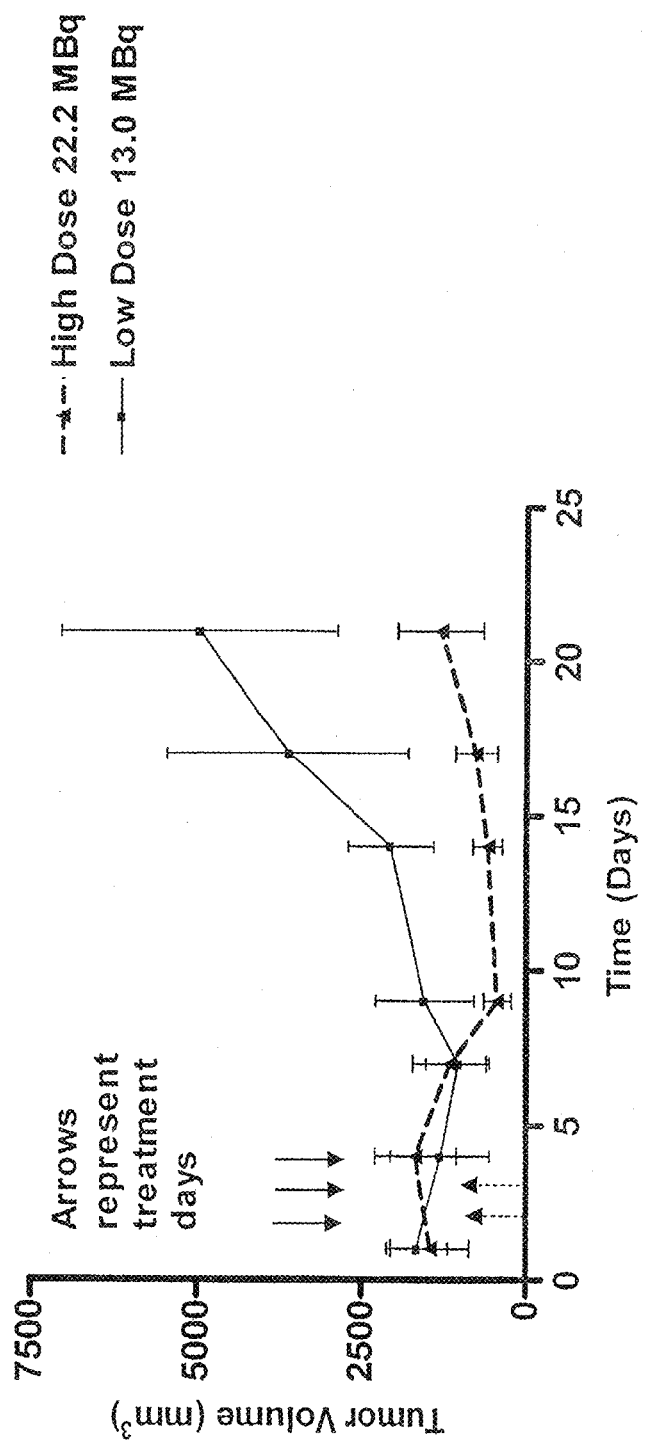
FIG. 17 shows a graph of large tumor volume bearing Lewis rats given high 22.2 MBq and low 13.0 MBq doses of $^{213}$Bi-DOTATOC. Symbols, means, Bars, SEM, Solid line with square symbol represents 13 MBq $^{213}$Bi-DOTATOC, Dashed line with the triangle symbol represents 22.2 MBq $^{213}$Bi-DOTATOC. Rats were treated for 3 consecutive days with $^{213}$Bi-DOTATOC.

A significant decrease in the rate of tumor growth was observed at 9 days PI in small volume tumor bearing rats (0.75 mm$^3$) treated with low-dose $^{213}$Bi-DOTATOC (12.6 MBq) as compared to controls (p<0.037) treated with only non-radioactive DOTATOC (FIG. 16). In the large-volume tumor bearing cohorts (1720 mm$^3$), rats receiving high-dose (22.2 MBq) $^{213}$Bi-DOTATOC showed significant tumor reduction (approximately 3×) at 9 days PI as compared to the rats receiving low-dose treatments (13 MBq) (p<0.025) (FIG. 17).

Tumor growth inhibition was observed in both small- and large-volume tumors when fractionated low- (12.6MBq) and high-dose (22.2MBq) $^{213}$Bi-DOTATOC were given, respectively. Previous reports indicate that the dose-limiting factor in PRRT is often nephrotoxicity caused by the radiation absorbed dose to the kidneys. Our results show only minimal nephrotoxicity observed with the low-dose $^{213}$Bi-DOTATOC (Table 1) and mild nephrotoxicity was observed with high-dose $^{213}$Bi-DOTATOC in only one animal. No significant changes in creatine clearance levels were observed in any of the treatment groups. The only evidence of other treatment induced toxicities observed was a slightly lower T4 value in the 13 MBq and the 22.2 MBq treatment groups at 25 days.

Enhancing Somatostatin Receptor Expression and Anticancer Therapy Using First and Second Therapeutic Agents Example 1

Cytotoxicity of Radiolabeled Somatostatin Analog

Figure 3:
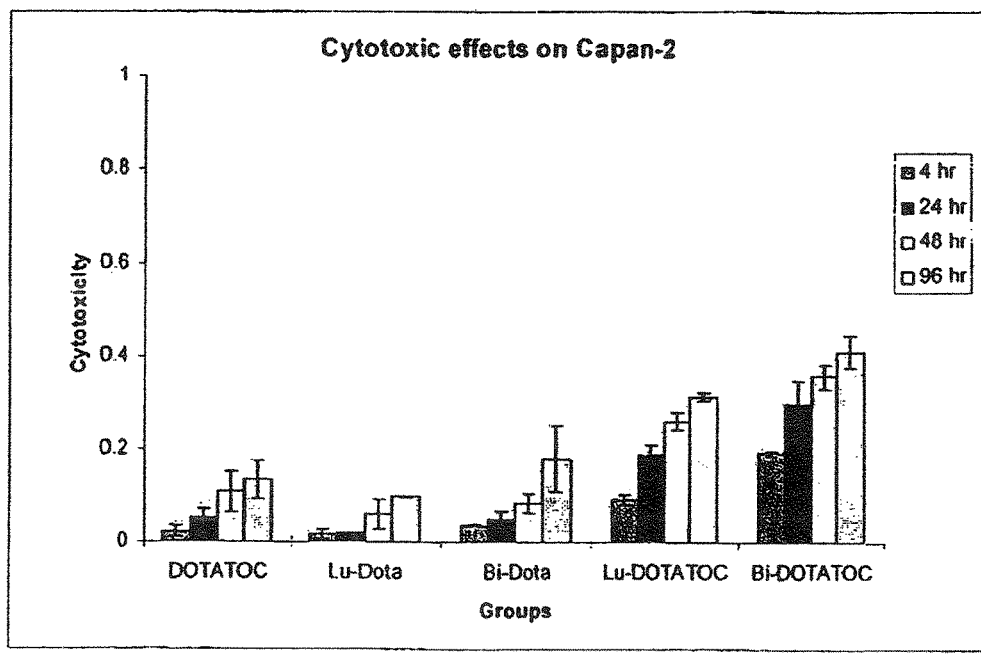
FIG. 3 provides a bar graph showing the cytotoxic effects of $^{177}$Lu and $^{213}$Bi labeled DOTA and DOTATOC on the somatostatin receptor expressing cell line Capan-2.
Figure 4:
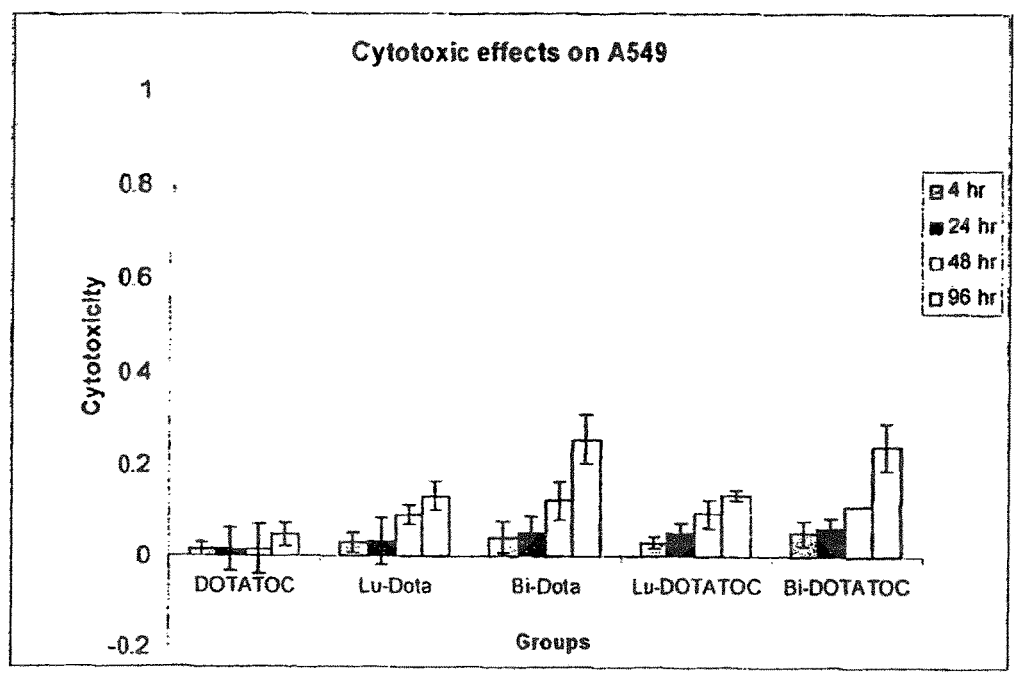
FIG. 4 provides a bar graph showing the cytotoxic effects of $^{177}$Lu and $^{213}$Bi labeled DOTA and DOTATOC on the somatostatin receptor negative cell line A549.

The somatostatin receptor (SSTr)-positive human pancreatic adenocarcinoma cell line Capan-2 was used as the test cell line, and the SSTr-negative human lung carcinoma cell line A549 was used as control cell line. Radiolabeled somatostatin analogs $^{213}$Bi-DOTATOC and $^{177}$Lu-DOTATOC were shown to be much more cytotoxic than non-somatostatin receptor-specific $^{213}$Bi-DOTA and $^{177}$Lu-DOTA in the somatostatin receptor expressing cell line Capan-2 (FIG. 3). However, when $^{213}$Bi-DOTATOC and $^{177}$Lu-DOTATOC cytotoxicity were compared with $^{213}$Bi-DOTA and $^{177}$Lu-DOTA cytotoxicity in somatostatin receptor negative cell line A549, no difference was observed (FIG. 4). FIG. 3 shows the cytotoxic effects of 37,000 becquerels (37 kBq) of $^{177}$Lu and $^{213}$Bi labeled to DOTA and DOTATOC on somatostatin receptor expressing cell line Capan-2. FIG. 4, on the other hand, shows the cytotoxic effects of 37 kBq of $^{177}$Lu and $^{2r3}$Bi labeled to DOTA and DOTATOC on somatostatin receptor negative cell line A549.

Example 2

Effects of Gemcitabine Pre-Treatment on Somatostatin Analog Cytotoxicity

Figure 5:
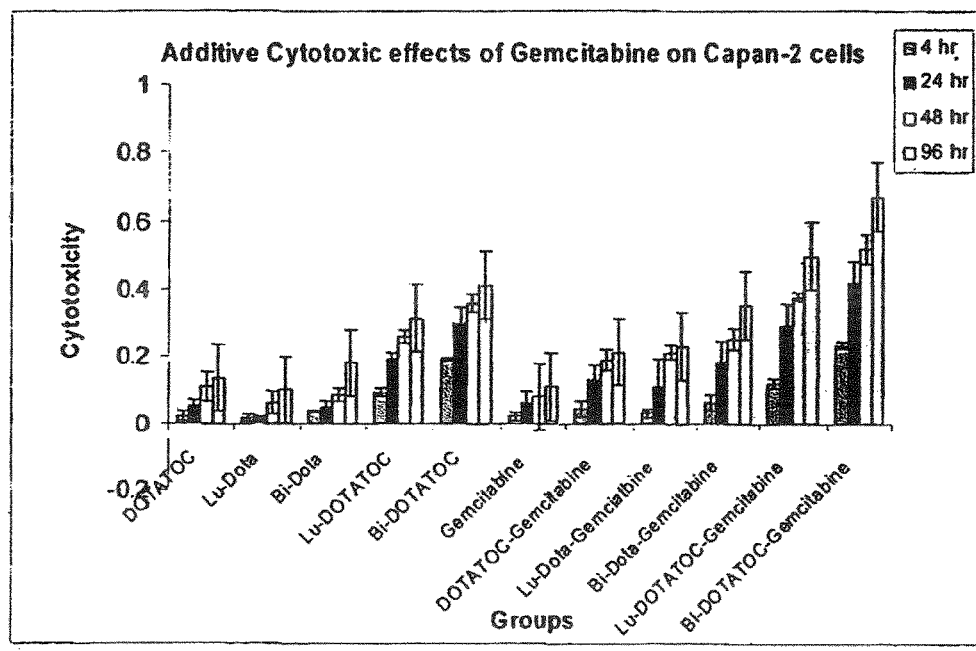
FIG. 5 provides a bar graph showing the cytotoxic effects of radionuclide labeled DOTA and DOTATOC in combination with gemcitabine pretreatment on the somatostatin receptor expressing cell line Capan-2.

One μg/mL Gemcitabine HCl was added to a somatostatin receptor expressing cell line (Capan-2) two hours prior to exposure to radiolabeled recognition ligand in order to evaluate the additive effects of gemcitabine when the cells were still exposed to gemcitabine and radionuclides. Note that this procedure is different from radiosensitivity studies where gemcitabine is washed off before the replenished cells are exposed to radiation. FIG. 5 shows the combined cytotoxic effects of 37 kBq of radionuclide labeled to DOTA and DOTATOC in combination with 1 μg/mL gemcitabine pre-treatment on somatostatin receptor expressing cell line Capan-2.

Example 3

Effects of Gemcitabine and Radiolabeled Somatostatin Analog on Apoptosis

Alpha emitters such as $^{213}$Bi are known to cause G$_2$M arrest and induce apoptosis in cancer cell lines. Experiments were thus performed to evaluate radiation-induced apoptosis and the radiobiological and radiotherapeutical relevance of this mode of cell death in selection of a radionuclide for therapy. The results are provided in FIG. 6, which shows the apoptotic effects of 37 kBq of $^{177}$Lu and $^{213}$Bi labeled to DOTA and DOTATOC on the somatostatin receptor expressing cell line Capan-2. As expected, high-linear energy transfer (LET) alpha emitter $^{213}$Bi exhibited much greater induction of apoptosis compared to that of the low-LET beta emitter $^{177}$Lu. At 48 hours, $^{213}$Bi-DOTATOC exhibited approximately 4 times greater induction of apoptosis than $^{177}$Lu-DOTATOC, and 100 times greater induction of apoptosis than non-radioactive DOTATOC.

Figure 6:
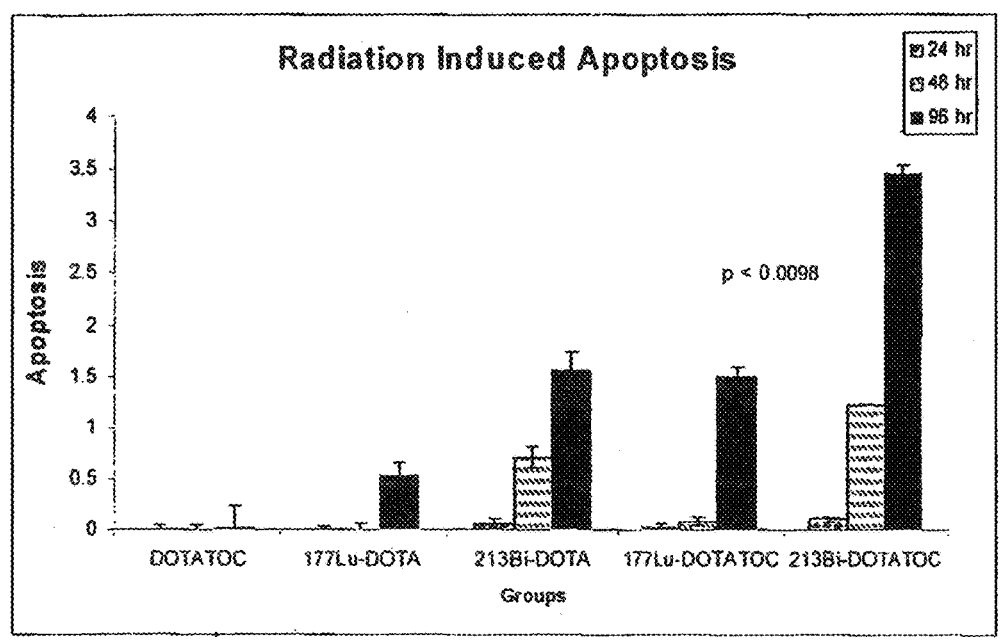
FIG. 6 provides a bar graph showing the apoptic effects of $^{177}$Lu and $^{213}$Bi labeled DOTA and DOTATOC on the somatostatin receptor expressing cell line Capan-2.

FIG. 6 also shows the effects of incubation time. For example, with $^{177}$Lu-DOTATOC, significant induction of apoptosis was observed at 96 hours, whereas almost similar induction of apoptosis was observed at 48 hours for $^{213}$Bi-DOTATOC, suggesting faster and greater induction of apoptosis by $^{213}$bismuth. Therefore, high-LET alpha emitter $^{213}$Bi labeled to DOTATOC is generally preferred for induction of apoptosis as compared to $^{177}$Lu labeled to DOTATOC (p>0.09).

Figure 7:
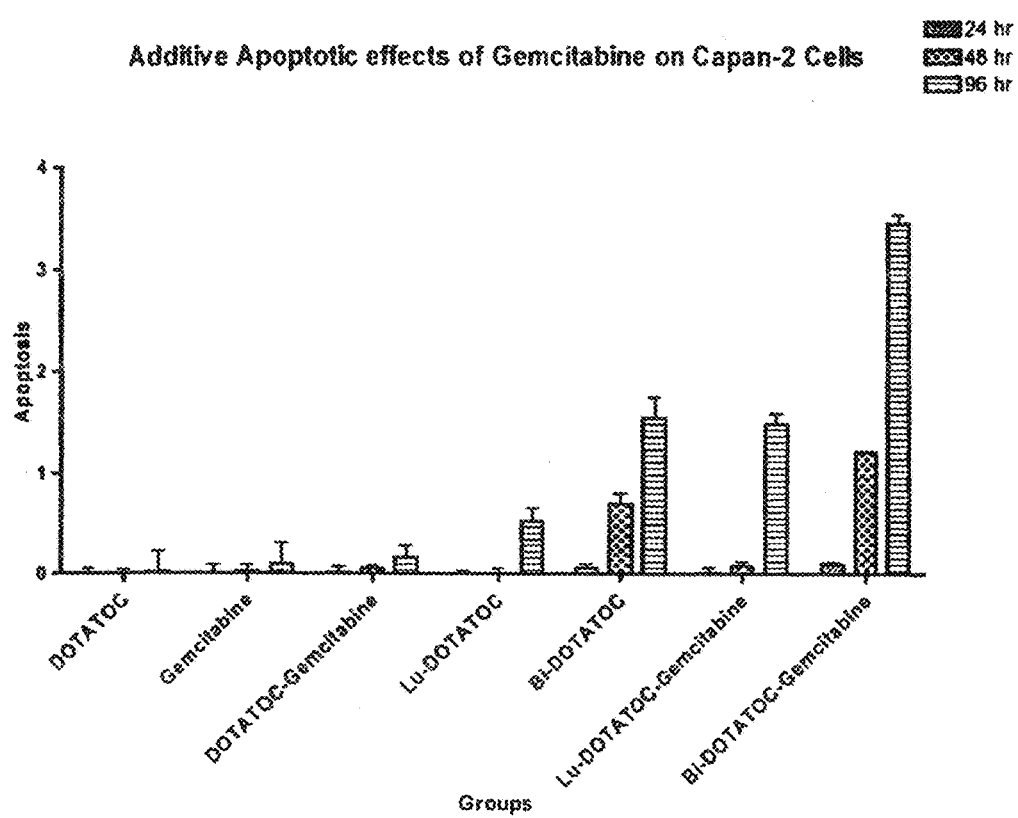
FIG. 7 provides a bar graph showing the apoptic effects of radionuclide labeled DOTA and DOTATOC in combination with gemcitabine pretreatment on the somatostatin receptor expressing cell line Capan-2

The effects of gemcitabine and a somatostatin analog on apoptosis are shown in FIG. 7. Activation or down regulation of pro- and anti-apoptotic genes influence cancer cell viability, cancer cell sensitivity to chemotherapy and radiotherapy, and tumor development and progression. A variety of chemotherapeutic agents induce cell death via apoptosis. Gemcitabine is known to induce apoptosis primarily due to Bax overexpression, whereas Bcl-xl is known to reduce gemcitabine-induced apoptosis. In contrast, Capan-2 is highly sensitive to Fas-mediated apoptosis. FIG. 7 shows the additive apoptotic effects of 37 kBq of radionuclide labeled to DOTA and DOTATOC in combination with 1 μg/mL gemcitabine pre-treatment on somatostatin receptor expressing cell line Capan-2. The data is expressed as ±S.E.M. of mean apoptosis. As shown in FIG. 7, gemcitabine by itself does not induce any significant amount of apoptosis. The same holds true for DOTATOC and gemcitabine combinations. But when combined with radiolabeled DOTATOC, a synergetic effect on induction of apoptosis is observed. For $^{177}$Lu-DOTATOC, this significant synergetic effect is observed at 96 hours, whereas for $^{213}$Bi-DOTATOC this effect is observed at 48 more and is much more pronounced at 96 hours.

Example 4

Gemcitabine Effect Somatostatin Receptor Expression and Re-Expression

Figure 8:
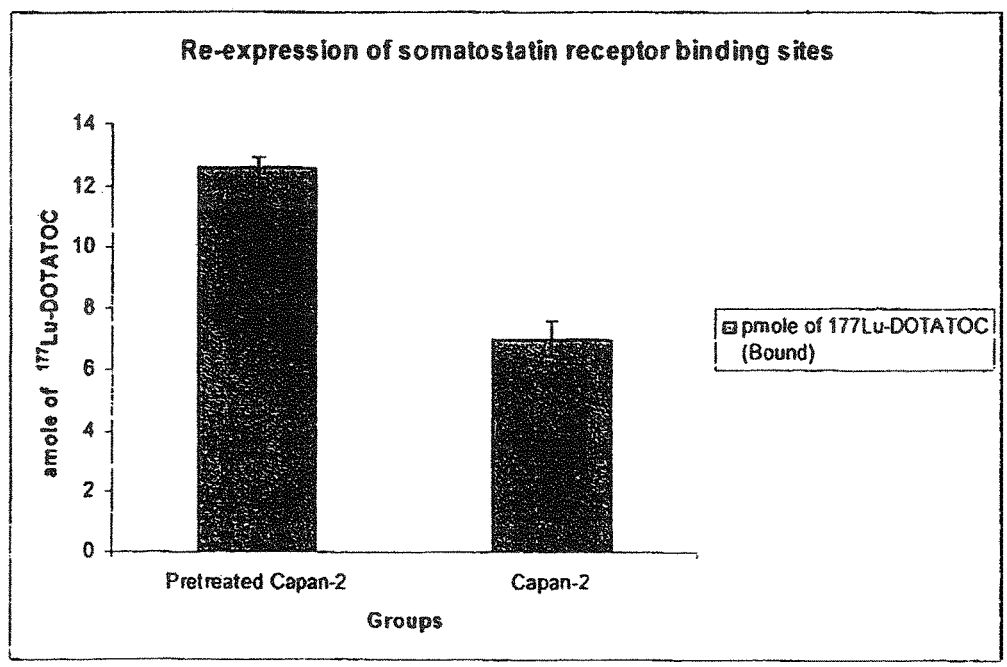
FIG. 8 provides a bar graph showing increased $^{177}$Lu-DOTATOC binding to gemcitabine pretreated Capan-2 cells.

A radioligand assay was performed to evaluate receptor binding by the recognition ligand after pre-treatment of 4 days with 1 µg/mL gemcitabine and 4 days of replenishment. FIG. 8 shows increased $^{177}$Lu-DOTATOC binding to gemcitabine pre-treated Capan-2 cells. As shown in FIG. 8, treatment with gemcitabine resulted in significant overexpression of binding sites, with almost 70% more binding sites than the non-treated Capan-2 cells.

The quantity of receptor ligand binding directly corresponds to the radiation dose given to the cells by the internalized $^{177}$Lu-DOTATOC. When compared to non-treated Capan-2 cells, the radiolabeled DOTATOC delivered around 150% more internalized dose to gemcitabine pro-treated Capan-2 cells, as shown in Table 1, which shows the increased $^{177}$Lu-DOTATOC internalized dose of gemcitabine pre-treated Capan-2 cells

TABLE 1

| Groups | $^{177}$Lu-DOTATOC % internalized |
| --- | --- |
| Gemcitabine pre-treated Capan-2 cells | 13.46 ± 0.033 |
| Capan-2 cells | 5.36 ± 0.053 |

The increased internalized dose to the cells would also influence the biological response of the cells to the treatment. To evaluate the corresponding biological response cell viability and apoptosis, assays were performed, as described in Example 5.

Example 5

Biological Response to Gemcitabine Pre-Treatment

Figure 9:
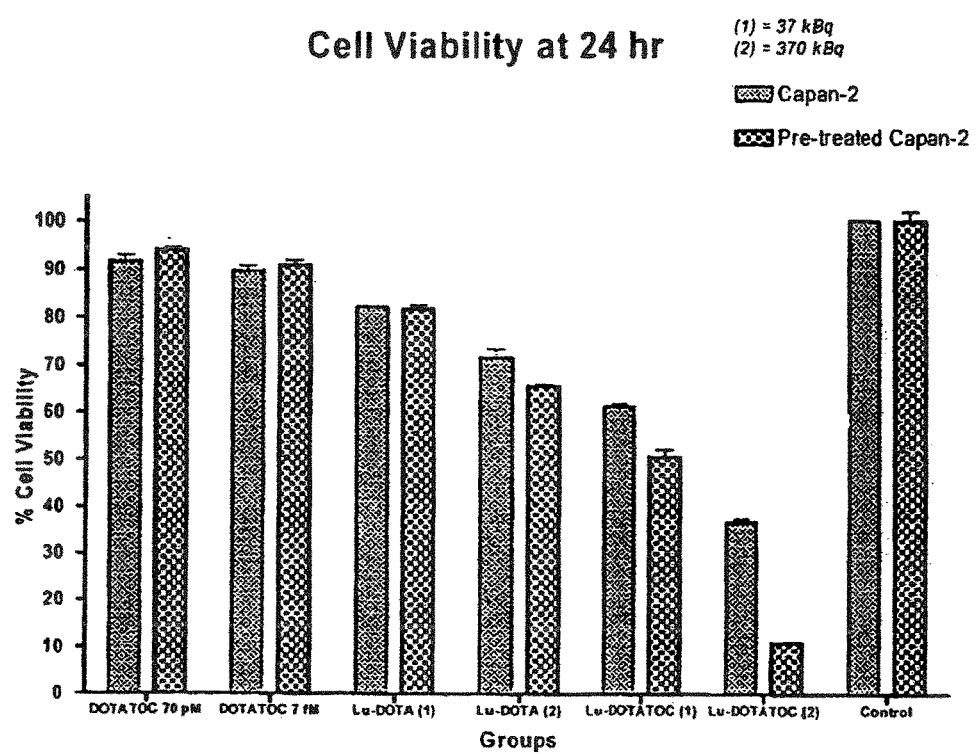
FIG. 9 provides a bar graph showing the increased effect of $^{177}$Lu-DOTATOC on cell viability at 24 hours for gemcitabine pretreated Capan-2 cells.

Effects of 37 kBq and 370 kBq of $^{177}$Lu labeled DOTATOC and DOTA on gemcitabine pre-treated Capan-2 cells and non-treated cells were evaluated using CellTiter-Glo® Luminescent Cell Viability Assay (Promega, Madison, Wis.) and Cell Death Detection ELISA$^{PLUS}$10× (Roche Applied Sciences, IN) for apoptosis. Cell viability was evaluated at 24 and 48 hours of incubations. FIG. 9 shows an increased $^{177}$Lu-DOTATOC effect on cell viability at 24 hours for gemcitabine pre-treated Capan-2 cells. From FIG. 9 at 24 hours, there were no significant effects observed for 70 pM and 7 fM DOTATOC on cell viability for gemcitabine pre-treated and non-treated Capan-2 cells. Effects of radiosensitivity induced by gemcitabine pre-treatment can be observed at higher doses (370 kBq) of non-target specific $^{177}$Lu-DOTA. For gemcitabine pre-treated Capan-2 cells, $^{177}$Lu-DOTATOC has a much pronounced and statistically significant effect on cell viability than non-treated Capan-2 cells (p<0.06). This effect is better expressed at higher doses (370 kBq) of $^{177}$Lu-DOTATOC, as demonstrated in FIG. 9.

Figure 10:
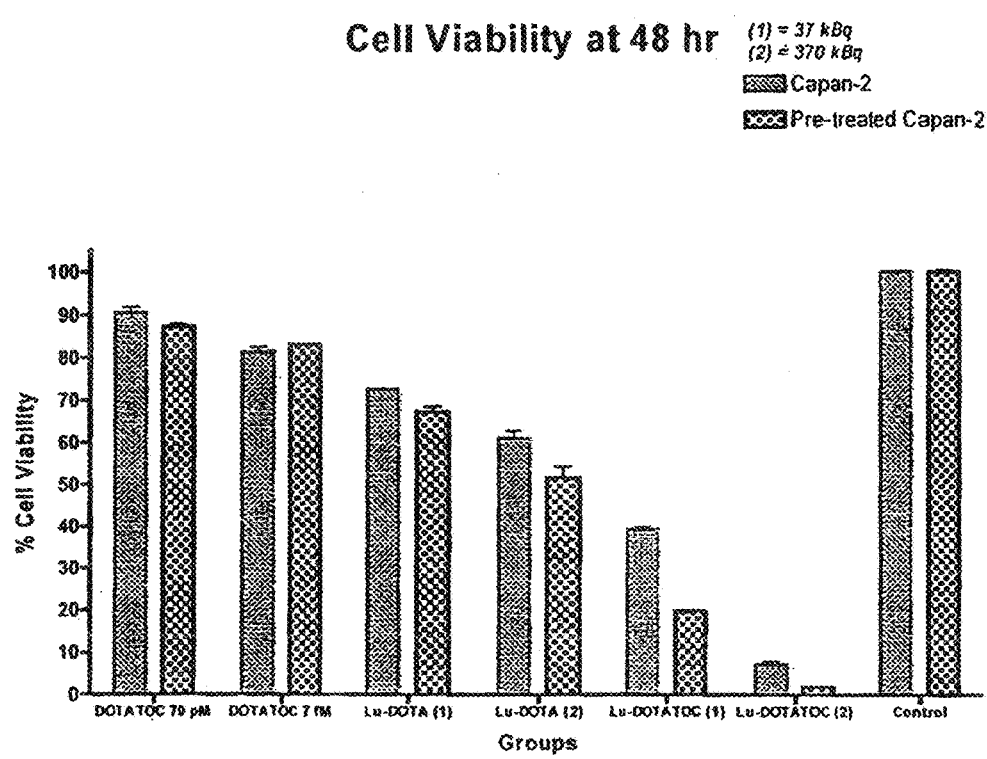
FIG. 10 provides a bar graph showing the increased effect of $^{177}$Lu-DOTATOC on cell viability at 48 hours for gemcitabine pretreated Capan-2 cells.

FIG. 10 shows the increased effect of $^{177}$Lu-DOTATOC on cell viability at 48 hours for gemcitabine pre-treated Capan-2 cells. As illustrated in FIG. 10, similar kinds of effects were observed after 48 hours for 70 pM and 7 fM DOTATOC. After 48 hours of incubation, effects of radiosensitivity induced by gemcitabine pre-treatment were observed at higher doses (370 kBq) as well as lower doses (37 kBq) of non-target specific $^{177}$Lu-DOTA, unlike the observations made after 24 hours of incubation. At the same time, the gemcitabine pre-treatment effects of higher doses of $^{177}$Lu-DOTATOC on cell viability was diminished compared to non-treated Capan-2 cells, whereas the gemcitabine pre-treatment effects were more pronounced for lower doses of $^{177}$Lu-DOTATOC, as shown in FIG. 10.

Figure 11:
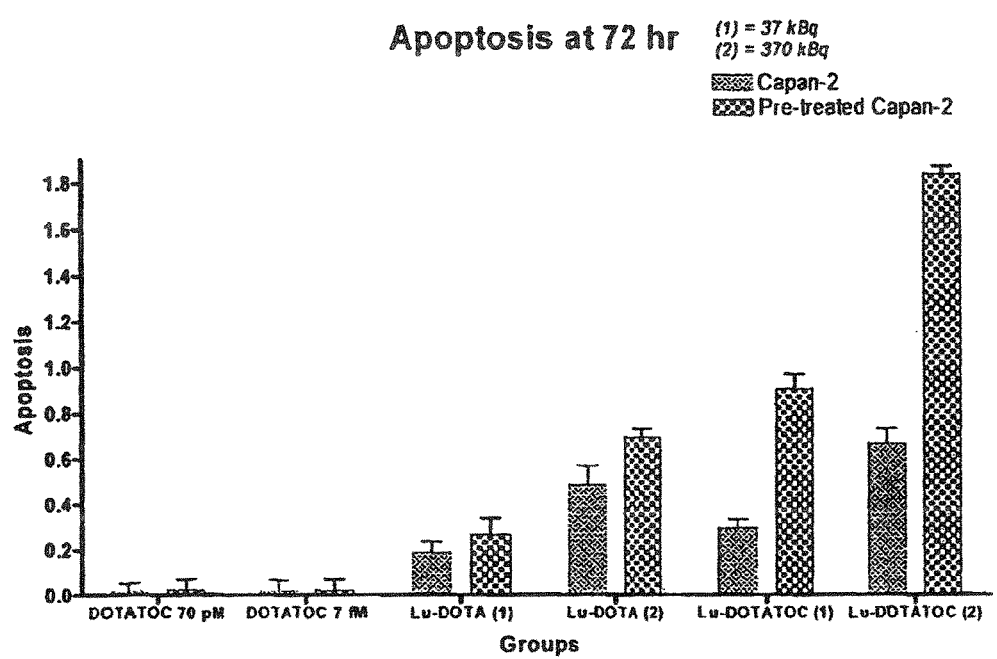
FIG. 11 provides a bar graph showing the increased effect of $^{177}$Lu-DOTATOC on apoptosis at 72 hours for gemcitabine pretreated Capan-2 cells.
Figure 12:
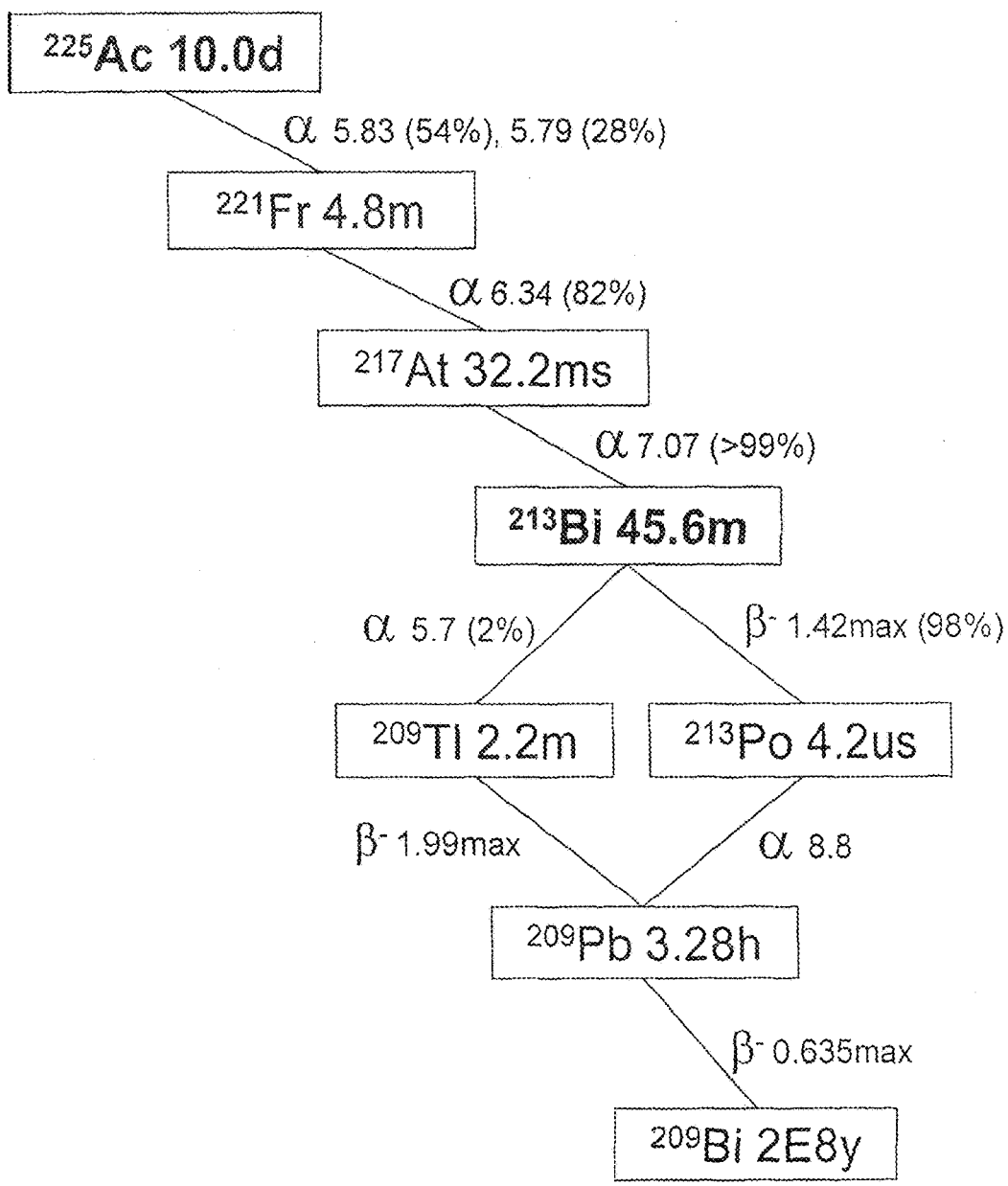
FIG. 12 shows the direct decay pathway (2%) of $^{213}$Bi by α-emission to the (3.980 MeV) β$^-$-particle emitter $^{209}$Tl.

FIG. 11 shows an increased $^{177}$Lu-DOTATOC effect on apoptosis at 72 hours for gemcitabine pre-treated Capan-2 cells. As shown by FIG. 11, DOTATOC without radiolabel had minimal effects on the induction of apoptosis. Enhancements of radiation induced apoptosis for non-target specific $^{177}$Lu-DOTA were observed for gemcitabine pre-treated Capan-2 cells as a result of possible radiosensitive phenomenon. For gemcitabine pre-treated Capan-2 cells, $^{177}$Lu-DOTATOC has a much pronounced and statistically significant effect on apoptosis than non-treated Capan-2 cells.

Summarizing the aspects of the invention provided by the examples, somatostatin receptor targeted radionuclide therapy using high-LET α-emitter $^{213}$Bi and low-LET β-emitter $^{177}$Lu labeled to DOTATOC show decreased cell survival, increased cell killing, and induction of apoptosis. $^{213}$Bi-DOTATOC is significantly more potent in vitro due to its high-LET α-emission and enhanced effects on mitotic and apoptotic deaths. Gemcitabine had overall additive and synergetic effects, with modulation and overexpression of somatostatin receptor binding sites after 4 days of pre-treatment. Data provided in the figures used in the examples above is generally expressed as ±S.E.M. of mean values.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference for all purposes. Any inconsistency between the material incorporated by reference and the material set for in the specification as originally filed shall be resolved in favor of the specification as originally filed. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A method of treating a somatostatin receptor expressing cancerous tumor in a patient in need, the method comprising administering to said patient an effective amount of a chelate-linked peptide analog of somatostatin comprising a radionuclide, wherein said peptide analog of somatostatin is Tyr$^3$-Octreotide, said chelate is 1,4,7,10-tetraazacyclododecane-1,4,7,10-tetraacetic acid (DOTA) and said radionuclide is the α particle emitter $^{213}$Bi, in a pharmaceutically acceptable carrier.

2. The method according to claim 1 wherein said cancerous tumor is a cancer of the breast, pancreas, stomach, prostate, kidney, colon, rectum, thyroid, lung, liver, brain or central nervous system or lymph system.

3. The method according to claim 2 wherein said cancerous tumor is a cancer of the breast, pancreas, prostate or thyroid.

4. The method according to claim 3 wherein said cancerous tumor is a cancer of the pancreas.

5. The method according to claim 1 wherein said cancerous tumor is a cancer of the stomach, kidney, colon, rectal, lung, liver, brain or central nervous system or lymph system.

6. The method according to claim 1 wherein said cancerous tumor is a cancer of the breast, pancreas, prostate, thyroid or brain or central nervous system.

7. The method according to claim 1 wherein said cancerous tumor is a cancer of the pancreas, prostate or breast.

8. The method according to claim 6 wherein said brain or central nervous system tumor is a meningioma, astrocytoma or glioma.

* * * * *

SEQUENCE LISTING

<160> NUMBER OF SEQ ID NOS: 1

<210> SEQ ID NO 1
<211> LENGTH: 14
<212> TYPE: PRT
<213> ORGANISM: Homo Sapiens
<220> FEATURE:

<400> SEQUENCE: 1

Ala Gly Cys Lys Asn Phe Phe Trp Lys Thr Phe Thr Ser Cys
1               5                   10